(12) United States Patent
Broder et al.

(10) Patent No.: US 12,037,164 B2
(45) Date of Patent: Jul. 16, 2024

(54) DEVICES AND METHODS FACILITATING SAMPLE TESTING

(71) Applicant: IDEXX Laboratories Inc., Westbrook, ME (US)

(72) Inventors: Daniel Howard Broder, South Portland, ME (US); Scott W. Wagner, York, ME (US)

(73) Assignee: IDEXX LABORATORIES INC., Westbrook, ME (US)

( * ) Notice: Subject to any disclaimer, the term of this patent is extended or adjusted under 35 U.S.C. 154(b) by 508 days.

(21) Appl. No.: 16/875,008

(22) Filed: May 15, 2020

(65) Prior Publication Data

US 2020/0361667 A1     Nov. 19, 2020

Related U.S. Application Data

(60) Provisional application No. 62/849,509, filed on May 17, 2019.

(51) Int. Cl.
*B65D 43/02*     (2006.01)
*C12M 1/00*     (2006.01)
*C12M 1/22*     (2006.01)

(52) U.S. Cl.
CPC ......... *B65D 43/0218* (2013.01); *C12M 23/10* (2013.01); *C12M 23/52* (2013.01);
(Continued)

(58) Field of Classification Search
CPC ............ B65D 43/0218; B65D 21/0209; B65D 21/0212; B65D 21/0217; B65D 21/0219;
(Continued)

(56) References Cited

U.S. PATENT DOCUMENTS 3,173,574 A * 3/1965 Goldsmith ........... B65D 21/022
                                                            206/508
3,729,382 A    4/1973 Shaffer et al.
(Continued)

FOREIGN PATENT DOCUMENTS

JP     S63-105669 A    5/1988
JP     H0657199 U     8/1994
(Continued)

OTHER PUBLICATIONS

International Preliminary Report on Patentability dated Nov. 16, 2021 by the International Bureau on behalf of the U.S. Patent and Trademark Office acting as International Searching Authority in International Application No. PCT/US2020/033058.
(Continued)

*Primary Examiner* — Jeffrey R Allen
(74) *Attorney, Agent, or Firm* — Carter, DeLuca & Farrell LLP

(57) ABSTRACT

A culture dish includes a base and a lid. The base includes a side wall and a concave floor that define a first interior volume open at a top end of the base. The base further includes an annular rim between the floor and a bottom end thereof. The lid includes a side wall and a ceiling that define a second interior volume open at a bottom end of the lid. The lid further includes an annular rim extending radially outwardly therefrom. An inner surface of the side wall of the lid is configured for slidable receipt about an outer surface of the side wall of the base to engage the lid about the base with the first and second interior volumes overlapping one another to define a sealed, combined internal volume bounded by the side walls of the base and the lid, the floor, and the ceiling.

29 Claims, 19 Drawing Sheets

(52) U.S. Cl.
CPC .............. *B65D 2543/00092* (2013.01); *B65D 2543/00296* (2013.01)

(58) Field of Classification Search
CPC .............. B65D 21/022; B65D 21/0222; B65D 21/0223; C12M 23/10
See application file for complete search history.

(56) References Cited

U.S. PATENT DOCUMENTS

| | | | | |
|---|---|---|---|---|
| 3,886,047 | A * | 5/1975 | Billups, Jr. ............ | C12M 23/46 435/305.3 |
| 6,602,704 | B1 * | 8/2003 | Maxwell ................ | C12M 23/38 435/305.4 |
| 2002/0045245 | A1 | 4/2002 | Copeland et al. | |
| 2005/0189362 | A1 * | 9/2005 | Muller ................ | B65D 43/0222 220/796 |
| 2008/0064090 | A1 * | 3/2008 | Whittlinger ........... | B01L 3/5085 435/305.3 |
| 2008/0085556 | A1 * | 4/2008 | Graefing ................ | C12M 23/12 435/303.1 |
| 2011/0174820 | A1 | 7/2011 | Giles | |

FOREIGN PATENT DOCUMENTS

| | | |
|---|---|---|
| JP | 2005087030 A | 4/2005 |
| JP | 2011-167187 A | 9/2011 |
| JP | 2017-503489 A | 2/2017 |

OTHER PUBLICATIONS

International Search Report and Written Opinion issued in corresponding International Application No. PCT/US2020/033058 dated Sep. 17, 2020, 17 pages.
Chinese Office Action issued in corresponding CN Patent Application No. 202080036446.3 dated Jan. 22, 2024, with English translation.
Notice of Reasons for Refusal issued by the Japanese Patent Office on May 21, 2024 in corresponding JP Patent Application No. 2021-568526, with English translation.

* cited by examiner

DEVICES AND METHODS FACILITATING SAMPLE TESTING

CROSS-REFERENCE TO RELATED APPLICATIONS

This application claims the benefit of and priority to U.S. Provisional Patent Application No. 62/849,509, filed on May 17, 2019, the entire contents of which are hereby incorporated herein by reference.

BACKGROUND

Technical Field

The present disclosure relates to sample testing and, more particularly, to devices and methods facilitating the testing of a sample, e.g., a water sample or other suitable sample, for microbial organisms.

Background of Related Art

Bacterial contamination is the major cause of water-borne infections in the world, resulting in gastroenteritis, diarrhea, cramps, vomiting, and fever. In underdeveloped countries, these infections kill millions of people annually.

The principle bacterial water-borne pathogens that have been shown to cause human disease include: *Salmonella* species; *Shigella dystenteriae; S. flexneri; S. sonnei; Vibrio cholerae; Leptospira* spp.; *Yersinia enterocolitica; Francisella tularensis; Escherichia coli*; and *Pseudomonas aeruginosa*.

Because of the importance of water as a natural resource and the impact of contamination by water-borne bacteria, it is important to test water samples specifically for the presence of such bacteria to determine the overall level of contamination and potential to harbor pathogenic microbes.

SUMMARY

Provided in accordance with aspects of the present disclosure is a culture dish including a lid and a base. The base defines a longitudinal axis and has a top end and a bottom end. The base includes a side wall, a floor, and an annular rim. The side wall extends from the top end of the base towards the bottom end of the base. The side wall includes an annular inner surface and an annular outer surface. The floor is supported by the side wall at a position disposed between the top and bottom ends of the base. The floor extends radially inwardly from the annular inner surface of the side wall and longitudinally towards the bottom end of the base. The floor has a concave surface facing the top end of the base and a convex surface facing the bottom end of the base. The concave surface of the floor and the annular inner surface of the side wall define a first interior volume that is open at the top end of the base. The annular rim extends from the side wall at a position disposed between the floor and the bottom end of the base. The lid defines a longitudinal axis and has a top end and a bottom end. The lid includes a side wall extending from the top end of the lid towards the bottom end of the lid. The side wall includes an annular inner surface and an annular outer surface. The lid further includes a ceiling disposed atop the side wall at the top end of the lid. The ceiling defines an inner surface facing the bottom end of the lid and an outer surface facing the top end of the lid. The inner surface of the ceiling and the annular inner surface of the side wall define a second interior volume that is open at the bottom end of the lid. The lid also includes an annular rim extending radially outwardly from the annular outer surface of the side wall. The inner annular surface of the side wall of the lid is configured for slidable receipt about the outer annular surface of the side wall of the base to engage the lid about the base with the first and second interior volumes at least partially overlapping one another to define a sealed, combined internal volume bounded by the side walls of the base and the lid, the floor, and the ceiling.

In an aspect of the present disclosure, the base is formed from an optically clear material and the lid is formed from an opaque material.

In another aspect of the present disclosure, the base is formed from a relatively hard material and the lid is formed from a relatively flexible material.

In yet another aspect of the present disclosure, the annular rim of the base includes a radial portion extending radially outwardly from the side wall and a longitudinal portion extending longitudinally from the side wall to the bottom end of the base. The annular rim surrounds a cylindrical volume.

In still another aspect of the present disclosure, an outer diameter of the annular rim of the lid is greater than an outer diameter of the ceiling to define a ring-shaped recess atop the annular rim of the lid and about the ceiling.

In still yet another aspect of the present disclosure, the ceiling is configured for receipt within the cylindrical volume of the longitudinal portion of the annular rim of the base with the longitudinal portion of the annular rim of the base disposed within the ring-shaped recess of the lid to stack the base on the lid.

In another aspect of the present disclosure, the inner annular surface of the side wall of the lid is disposed at a first angle and the outer annular surface of the side wall of the base is disposed at a second angle different from the first angle.

In another aspect of the present disclosure, the annular rims of the lid and base define finger holds configured to facilitate manipulation, engagement, and disengagement of the lid and base.

In still another aspect of the present disclosure, in a bottomed-out condition, corresponding to a fully engaged position of the lid about the base, the side wall of the base abuts the ceiling of the lid and/or the side wall of the lid abuts the annular rim of the base.

In yet another aspect of the present disclosure, in a bottomed-out condition, corresponding to a fully engaged position of the lid about the base, the side wall of the base abuts the ceiling of the lid and the side wall of the lid is spaced from the annular rim of the base.

Another culture dish provided in accordance with aspects of the present disclosure includes a base and a lid. The base defines a longitudinal axis and has a top end and a bottom end. The base further includes a side wall including an annular inner surface and an annular outer surface, and a floor supported by the side wall at a position disposed between the top and bottom ends of the base. The lid defines a longitudinal axis and has a top end and a bottom end. The lid includes a side wall including an annular inner surface and an annular outer surface, and a ceiling disposed atop the side wall at the top end of the lid. One of the base or the lid defines a relatively hard configuration and the other of the base or the lid defines a relatively flexible configuration. The inner annular surface of the side wall of the lid is configured for slidable receipt about the outer annular surface of the side wall of the base. The relatively flexible one of the base or the lid is configured to flex to enable slidable receipt of the inner annular surface of the side wall of the lid about the outer annular surface of the side wall of the base and to sealingly engage the lid about the base.

In an aspect of the present disclosure, the base defines the relatively hard configuration and the lid defines the relatively flexible configuration. In such embodiments, the base may be formed from hard polystyrene and/or the lid may be formed from low density polyethylene.

In still another aspect of the present disclosure, the base and/or the lid is formed from a material having a high oxygen permeability and a low permeability for water vapor.

In yet another aspect of the present disclosure, the base and/or the lid includes an annular rim extending from the respective side wall thereof. The annular rim(s) defines a finger hold configured to facilitate manipulation, engagement, and disengagement of the base and/or the lid.

In still yet another aspect of the present disclosure, the base includes an annular rim extending from the side wall thereof and the ceiling of the lid is configured for at least partial receipt within the annular rim of the base to stack the base on the lid.

A method of determining the presence or absence of microbial organisms in a sample is also provided in accordance with aspects of the present disclosure. The method includes obtaining a culture dish. The culture dish may include any or all of the features of the culture dishes detailed above or otherwise herein. In aspects, the culture dish includes a base and a lid. The base includes a side wall and a floor supported by the side wall. The floor has a concave surface facing an open top end of the base and a convex surface facing a bottom end of the base. The lid includes a side wall and a ceiling disposed atop the side wall at a top end of the lid. The ceiling defines an inner surface facing a bottom end of the lid and an outer surface facing the top end of the lid. The lid is engaged about the base with an inner annular surface of the side wall of the lid disposed about an outer annular surface of the side wall of the base to define a sealed internal volume bounded by the side walls of the base and the lid, the floor, and the ceiling.

The method further includes disengaging the lid from the base, pouring a sample into the base such that the sample is distributed across the concave surface of the floor, approximating the lid relative to the base such that the inner annular surface of the side wall of the lid is slid into sealed engagement about the outer annular surface of the side wall of the base to sealingly enclose the sample within the sealed internal volume, incubating the culture dish, and counting any bacterial colonies formed within the sealed internal volume.

In an aspect of the present disclosure, a growth medium is disposed within the base or introduced into the base prior to pouring the sample into the base.

In another aspect of the present disclosure, pouring the sample includes pouring the sample onto the growth medium.

In yet another aspect of the present disclosure, counting any bacterial colonies includes looking through the base and utilizing the cover as a backdrop.

In still another aspect of the present disclosure, the side wall of the lid is flexed as the inner annular surface of the side wall of the lid is slid into sealed engagement about the outer annular surface of the side wall of the base.

In still yet another aspect of the present disclosure, the inner annular surface of the side wall of the lid is disposed at a first angle and the outer annular surface of the side wall of the base is disposed at a second, different angle such that as the inner annular surface of the side wall of the lid is progressively slid into sealed engagement about the outer annular surface of the side wall, a strength of the engagement therebetween is progressively increased.

In another aspect of the present disclosure, incubating the culture dish includes permitting oxygen to permeate through at least one of the lid or the base into the sealed internal volume and inhibiting water vapor from permeating through the lid or the base from the sealed internal volume.

In still another aspect of the present disclosure, the method further includes stacking the culture dish atop another culture dish and/or stacking another culture dish atop the culture dish.

In another aspect of the present disclosure, the method further includes inverting the culture dish such that the culture dish is supported by the lid. The culture dish may be inverted prior to incubation or prior to counting.

In yet another aspect of the present disclosure, disengaging the lid from the base includes grasping annular rims associated with the lid and the base and pulling at least one of the lid or the base apart from the other. Additionally or alternatively, approximating the lid relative to the base to sealingly enclose the sample within the sealed internal volume includes grasping annular rims associated with the lid and the base and pushing at least one of the lid or the base towards the other.

In still another aspect of the present disclosure, approximating the lid relative to the base further includes bottoming-out the lid against the base and/or the base against the lid.

BRIEF DESCRIPTION OF THE DRAWINGS

Various aspects and features of the present disclosure are described herein with reference to the drawings wherein like reference numerals identified similar or identical elements.

DETAILED DESCRIPTION

Figure 1:
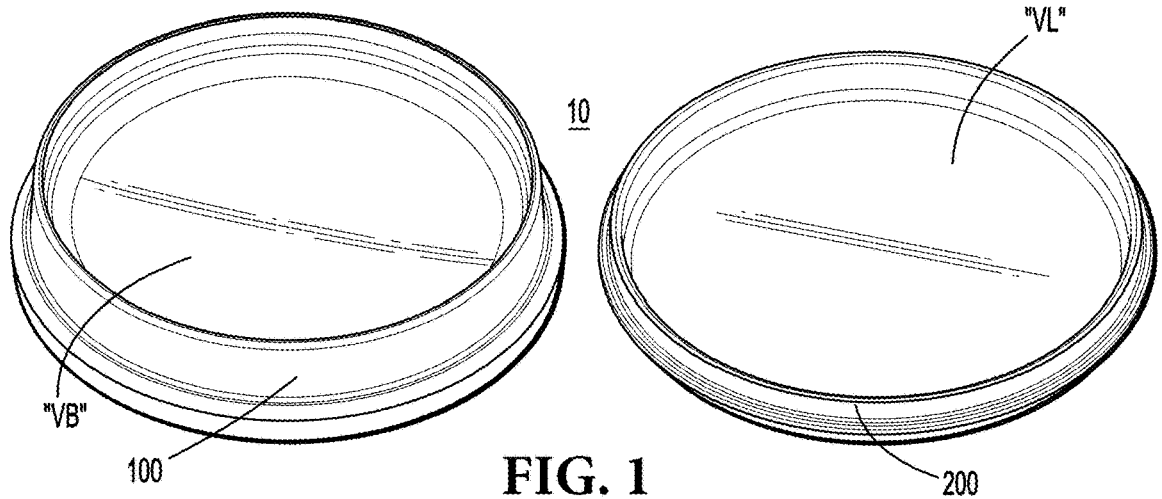
FIG. 1 illustrates a culture dish provided in accordance with the present disclosure including a top, perspective view of a base of the culture dish and a bottom perspective view of a lid of the culture dish, wherein the lid is removed from the base.
Figure 2:
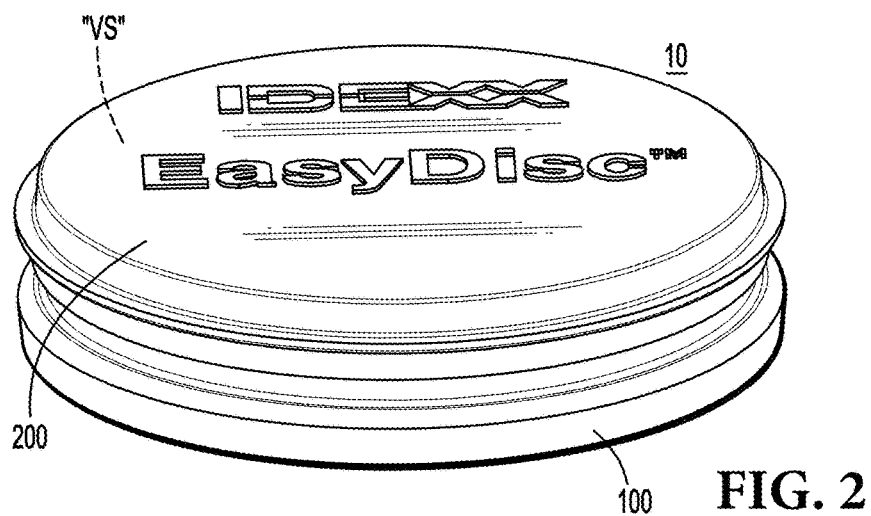
FIG. 2 is a top, perspective view of the culture dish of FIG. 1 with the lid engaged on the base.
Figure 3:
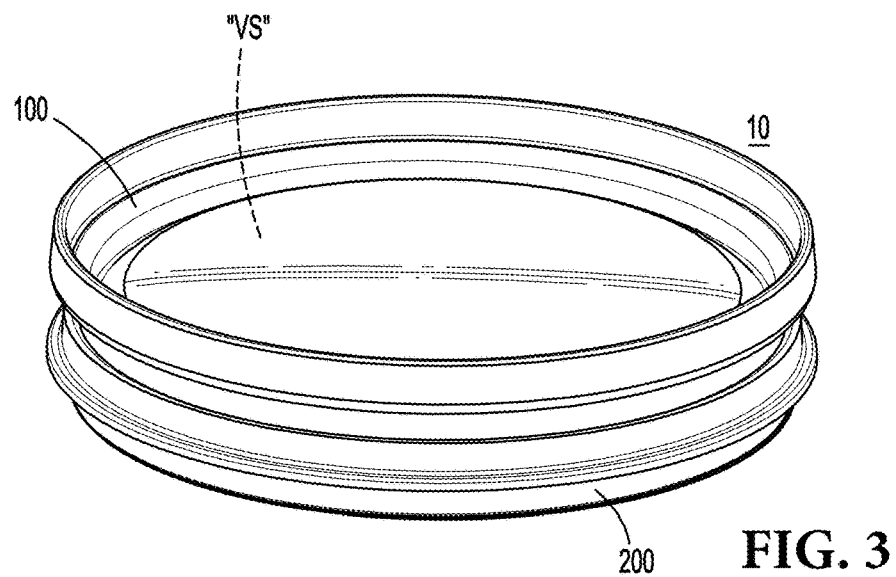
FIG. 3 is a bottom, perspective view of the culture dish of FIG. 1 with the lid engaged on the base.
Figure 4A:
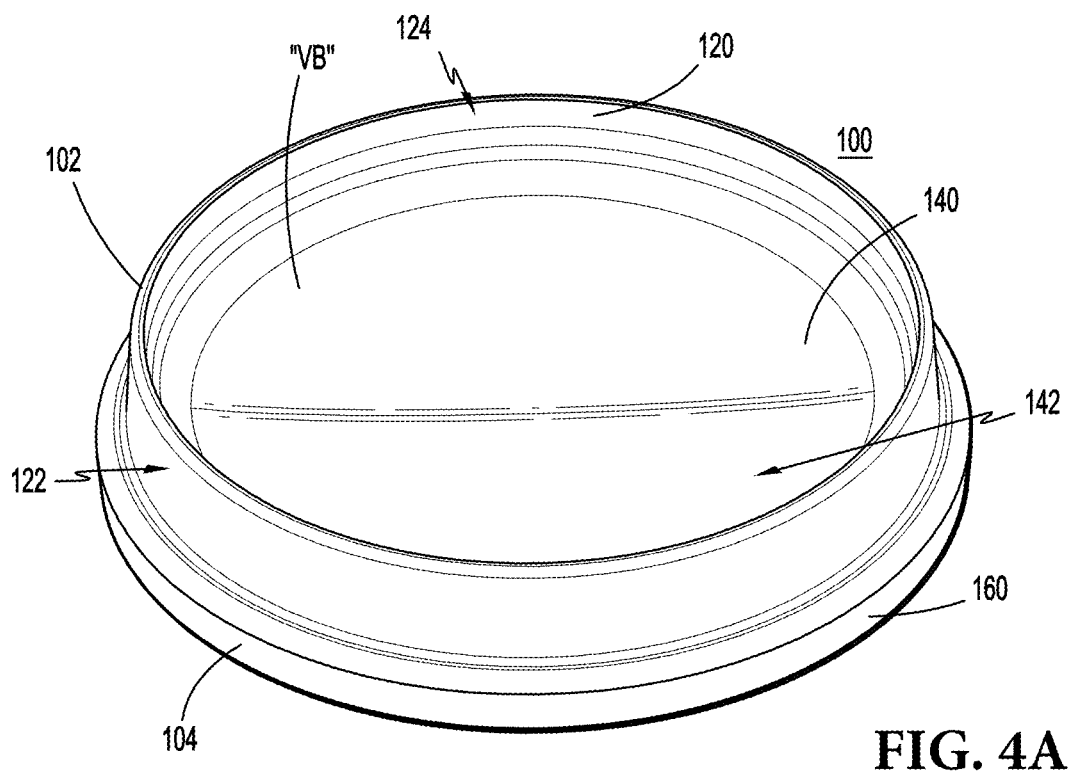
FIGS. 4A and 4B are respective top and bottom perspective views of the base of the culture dish of FIG. 1.
Figure 4B:
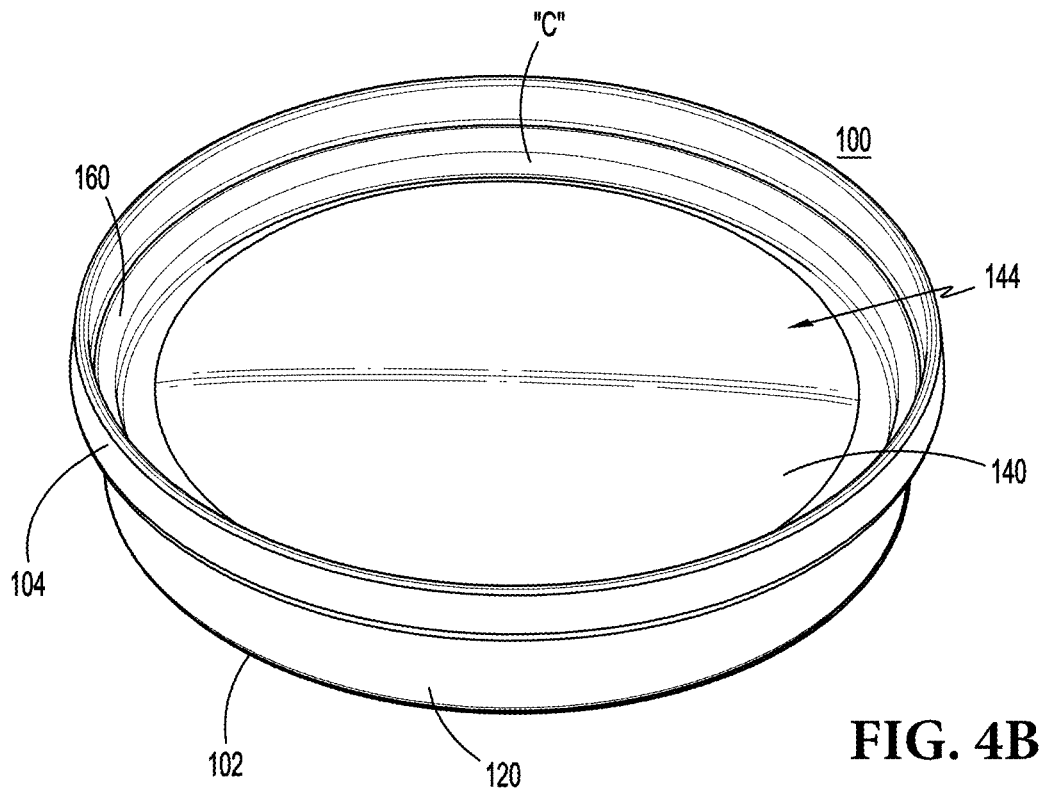
Figure 14:
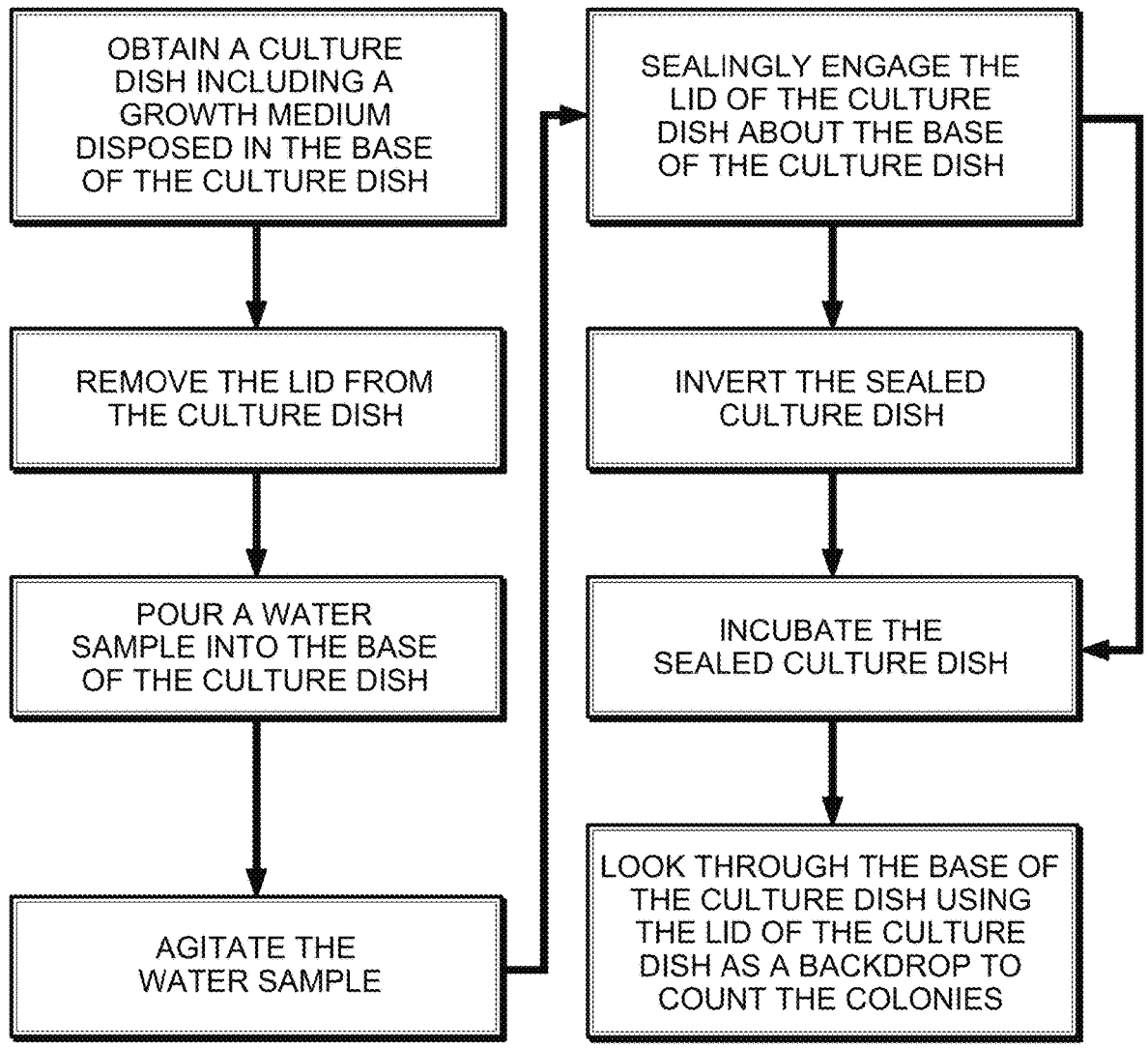
FIG. 14 is a flow diagram illustrating a method of determining the presence or absence of microbial organisms in a water sample in accordance with the present disclosure.

Referring generally to FIGS. 1-3, the present disclosure provides a culture dish, generally identified by reference numeral 10, and a method of testing a sample, e.g., a water sample, using the same (see FIG. 14). Other suitable samples to be tested may include, for example: beverages, milk, meat juices, food, environmental samples, pharmaceuticals, urine, sputum, semen, tissues, a swab or swabbing, blood, serum, and plasma. Culture dish 10 includes a base 100 and a lid 200. Culture dish 10 facilitates manipulation of lid 200 and base 100 (as separate components and when engaged with one another), pouring growth medium and/or a test sample into base 100 (although it contemplated, as detailed below, that the growth medium be disposed within base 100 during manufacturing), sealing engagement of lid 200 with base 100, disengagement of lid 200 from base 100, stacking of plural culture dishes 10 atop one another, incubation, and counting the number of resultant bacterial colonies after incubation.

Turning to FIGS. 4A-8, base 100 is formed as a single, monolithic piece of material from molding or other suitable process. Base 100 is formed from an optically clear material to enable visualization therethrough. In embodiments, the material forming base 100 has a "high" oxygen permeability while having a "low" permeability for water vapor. Oxygen permeability may be beneficial in promoting the growth of aerobic microbes or facultatively aerobic microbes. A "high" oxygen permeability of base 100 for the purposes herein is considered an oxygen transmission rate, measured in 25 µg/m$^2$/24 h, in embodiments, of at least 2000, in other embodiments, of at least 3000, and in still other embodiments, of at least 4000. A "low" permeability for water vapor of base 100 for the purposes herein is considered a water vapor transmission rate, measured in 25 µg/m$^2$/24 h, in embodiments, of no greater than 200, in other embodiments, no greater than 170, and in still other embodiments, no greater than 140. Further, in embodiments, the material forming base 100 has a relatively high oxygen permeability and a relatively low permeability for water vapor, wherein such relativity for the purposes herein is considered a ratio of oxygen permeability to water vapor permeability of, in embodiments, of at least 10:1, in other embodiments, at least 20:1 and, in still other embodiments, at least 30:1.

Base 100 is formed from a relatively hard material. The relatively hard base 100 is configured with sufficient hardness to inhibit significant deformation of base 100 during use, without being too brittle such that base 100 may break during normal use, e.g., when placed on a surface, when stacked on or stacked upon, when lid is engaged/disengaged, etc.

One suitable material meeting the above criteria is hard polystyrene, although other suitable materials are also contemplated, e.g., polycarbonate, acrylic, cyclic olefin polymer (COP), or urethane. In embodiments where base 100 is formed from polystyrene, at least a portion of base 100, e.g., floor 140 and/or the interior surface of side wall 120, or the entirety thereof, may be plasma-treated to increase the surface energy of the polystyrene, thereby reducing hydrophobicity (thus making the polystyrene more hydrophilic). Such a configuration promotes adherence of the growth medium to base 100 which, as detailed below, may be dried to base 100 during manufacturing. This configuration may additionally or alternatively, facilitate pouring the test sample and/or growth medium (in embodiments where the growth medium is poured into base 100 by a user rather than disposed within base 100 during manufacturing) into and distributing the same within base 100. In embodiments where base 100 is formed from a different material, plasma treating may likewise be utilized for similar purposes.

Continuing with reference to FIGS. 4A-8, base 100 defines a top end 102 and a bottom end 104 and includes a side wall 120, a floor 140, and an annular rim 160. Side wall 120 defines a generally cylindrical configuration and is open at top end 102 of base 100. Floor 140 is supported by and depends from side wall 120 at an intermediate position between top and bottom ends 102, 104, respectively, of base 100. Annular rim 160 extends from side wall 120 at bottom end 104 of base 100.

Figures 7, 8:
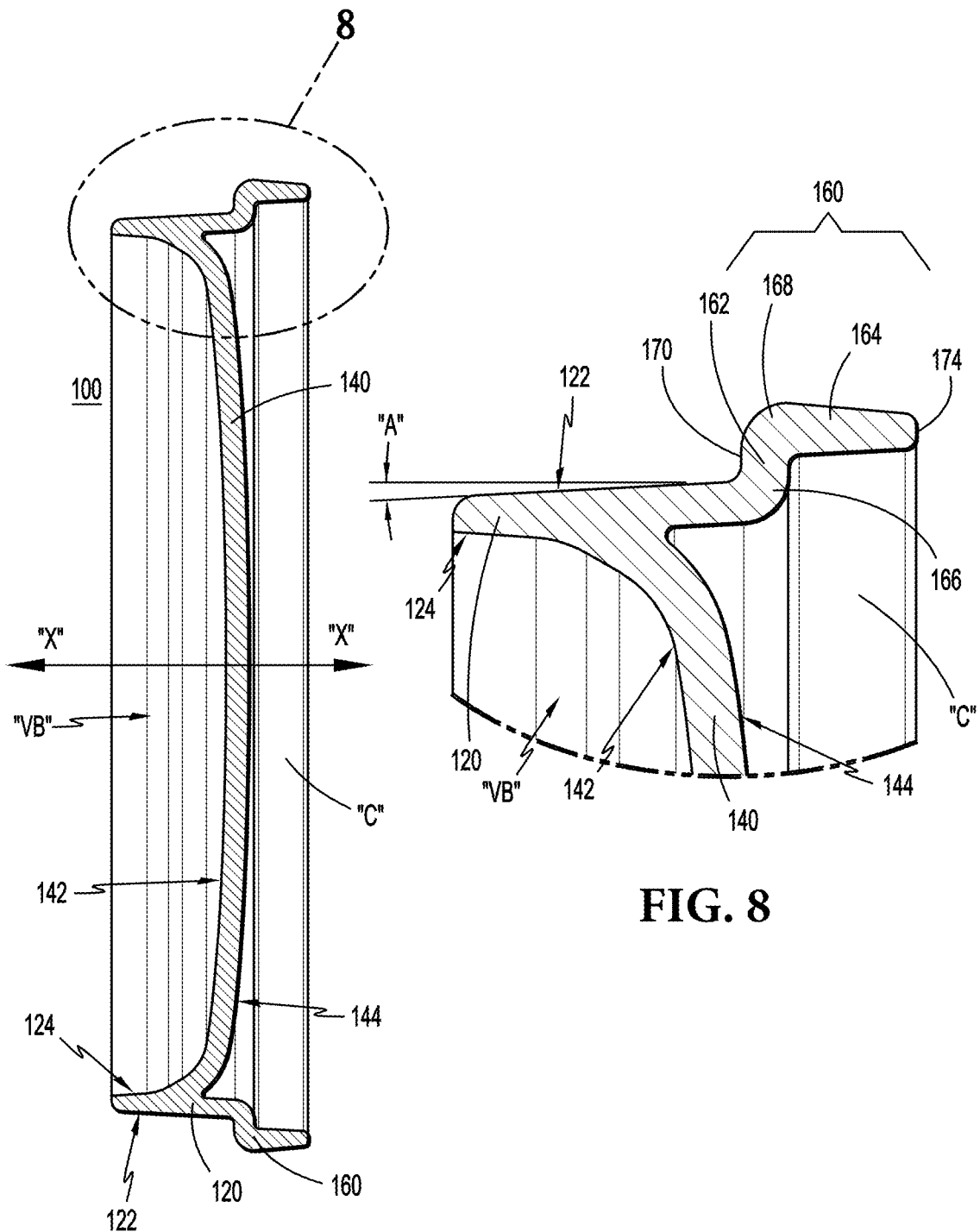
FIG. 7 is a cross-sectional view taken along section line "7-7" of FIG. 6.
FIG. 8 is an enlarged, cross-sectional view of the area of detail indicated as "8" in FIG. 7.

Side wall 120, as noted above, defines a generally cylindrical configuration. Side wall 120 surrounds a cylindrical volume having a circular transverse cross-section. However, side wall 120 is not perfectly cylindrical, in embodiments. Rather, in such embodiments, outer annular surface 122 of side wall 120 tapers radially inwardly in a bottom-to-top direction along at least a portion of the length of side wall 120, e.g., from bottom end 104 of base to top end 102 thereof. Referring momentarily to FIGS. 7 and 8, outer annular surface 122 of side wall 120 may be angled relative to (rather than parallel to) the longitudinal axis "X" of base 100. More specifically, outer annular surface 122 is angled radially inwardly off of parallel at an angle "A" in a bottom-to-top direction. The angle "A," in embodiments, may be from 2 degrees to 4 degrees, in embodiments, from 2.5 degrees to 3.5 degrees and, in still other embodiments, 3 degrees.

Referring again to FIGS. 4A-8, floor 140 of base 100, as noted above is supported by and depends from side wall 120 at an intermediate position between top and bottom ends 102, 104, respectively, of base 100. More specifically, floor 140 extends radially inwardly and towards bottom end 104 of base 100 from an inner annular surface 124 of side wall 120. Floor 140 defines a radially-symmetric, e.g., centered about longitudinal axis "X," concave surface 142 that faces towards top end 102 of base 100. As such, the nadir of floor 140 is centered on longitudinal axis "X." Floor 140 conversely defines a radially-symmetric, e.g., centered about longitudinal axis "X," convex surface 144 that faces towards bottom end 104 of base 100 with the apex thereof centered on longitudinal axis "X."

The above-detailed configuration of side wall 120 and floor 140 defines an internal volume "VB" bounded radially by inner annular surface 124 of side wall 120 and towards bottom end 104 of base 100 by concave surface 142 of floor 140. Top end 102 of base 100 is open, thus providing access to the internal volume "VB" to permit pouring of a test sample (and, in embodiments, the growth medium) into internal volume "VB." Concave bottom surface 142 of internal volume "VB" facilitates pouring and distributing of the sample (and, in embodiments, the growth medium) by inhibiting or reducing meniscus formation resulting in uneven distribution wherein the sample (and/or medium) builds up about the annular perimeter, e.g., against inner annular surface 124. In other embodiments, as an alternative to concave bottom surface 142, bottom surface 142 may be slanted, define different depths, define different pitches, etc. Base 100 is configured such that the surface area of concave bottom surface 142 enables a 1 mL sample, e.g., water, to be evenly distributed thereabout. Of course, for other sample volumes, base 100 may be differently configured to enable a different size test sample to be evenly distributed about concave bottom surface 142.

Figure 5:
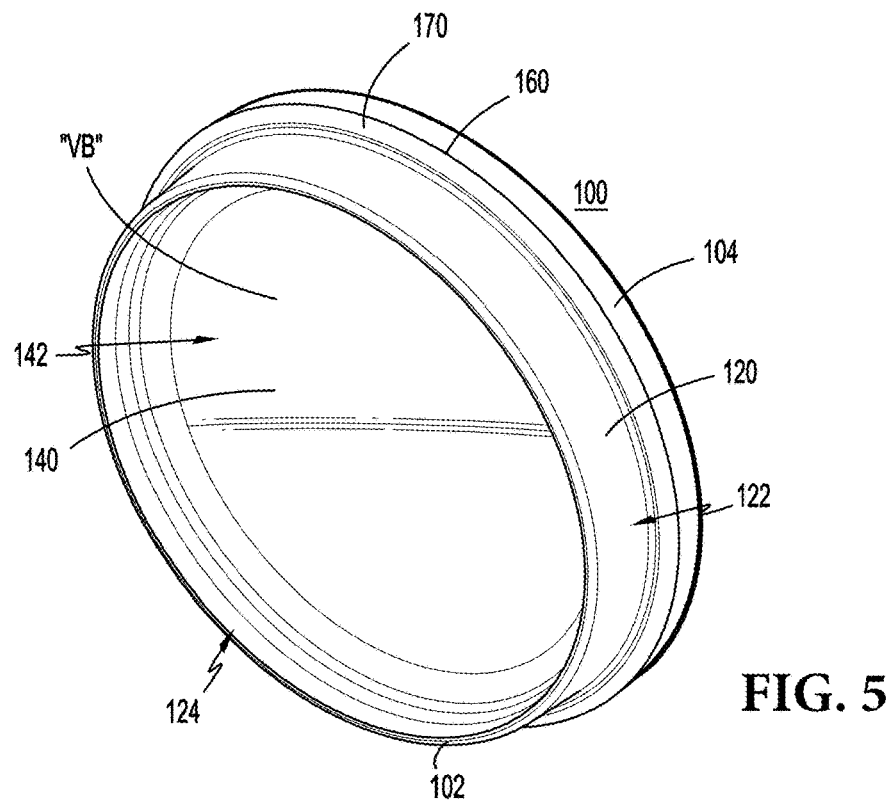
FIG. 5 is a side, perspective view of the base of the culture dish of FIG. 1.
Figure 6:
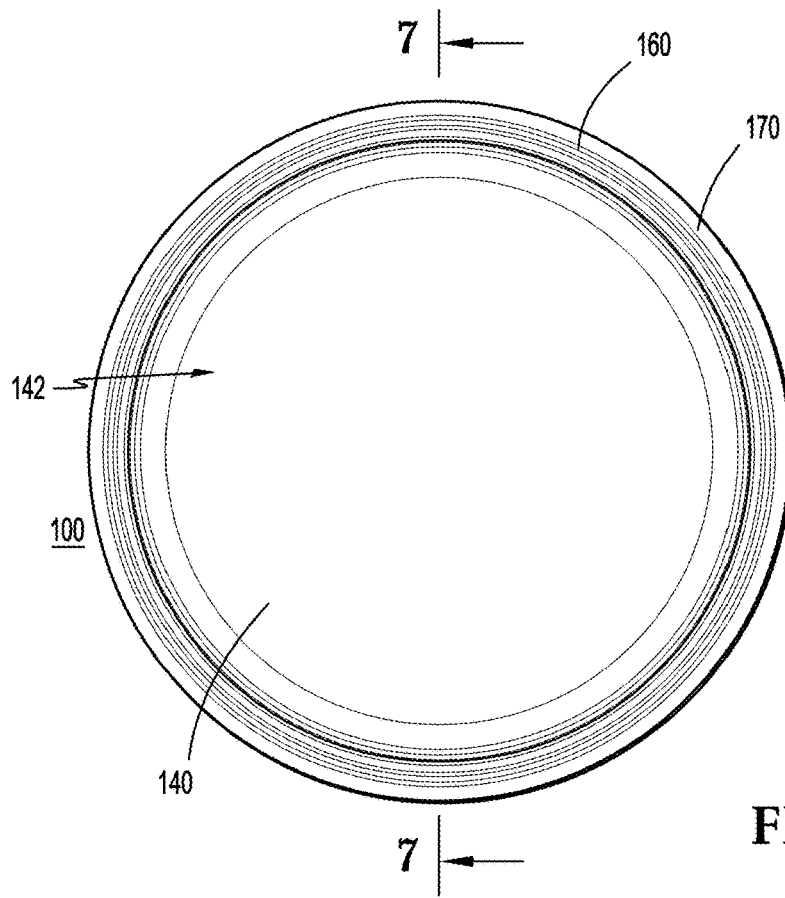
FIG. 6 is a top view of the base of the culture dish of FIG. 1.

With reference to FIG. 8, in conjunction with FIGS. 5-7, annular rim 160 of base extends from side wall 120 at bottom end 104 of base 100. Annular rim 160, more specifically, includes a radial portion 162 extending radially outwardly relative to side wall 120 at bottom end 104 of base, and a longitudinal portion 164 extending longitudinally away from side wall 120. A first elbow 166 interconnects side wall 120 and radial portion 162 of annular rim 160 and a second elbow 168 interconnects radial portion of annular rim 160 with longitudinal portion 164 of annular rim 160. As a result of this configuration, annular rim 160 includes an annular shelf 170 facing towards top end 102 of base 100. Annular shelf 170 defines an upper surface lying within a plane that extend perpendicularly relative to longitudinal axis "X."

A free end 174 of longitudinal portion 164 of annular rim 160 defines a support edge upon which base 100 is configured to be supported on a surface, e.g., a table, shelf, etc. In this manner, floor 140 is supported above and spaced-apart from the surface. A cylindrical area "C" is defined radially within longitudinal portion 164 of annular rim 160 and longitudinally between free end 174 of longitudinal portion 164 of annular rim 160 and second elbow 168 of annular rim 160. An additional area is defined radially within side wall 120 and longitudinally between convex surface 144 of floor 140 and first elbow 166 of annular rim 160. This additional area defines a diameter less than the diameter of cylindrical area "C." Further, this additional area is irregular due to the convex configuration of floor 140. Convex surface 144 of floor 140 does not extend beyond the bottom end of side wall 120 and, thus, does not extend beyond the additional area into cylindrical area "C."

Figure 9:
FIG. 9 is a top perspective view of the lid of the culture dish of FIG. 1, including markings.
Figure 9A:
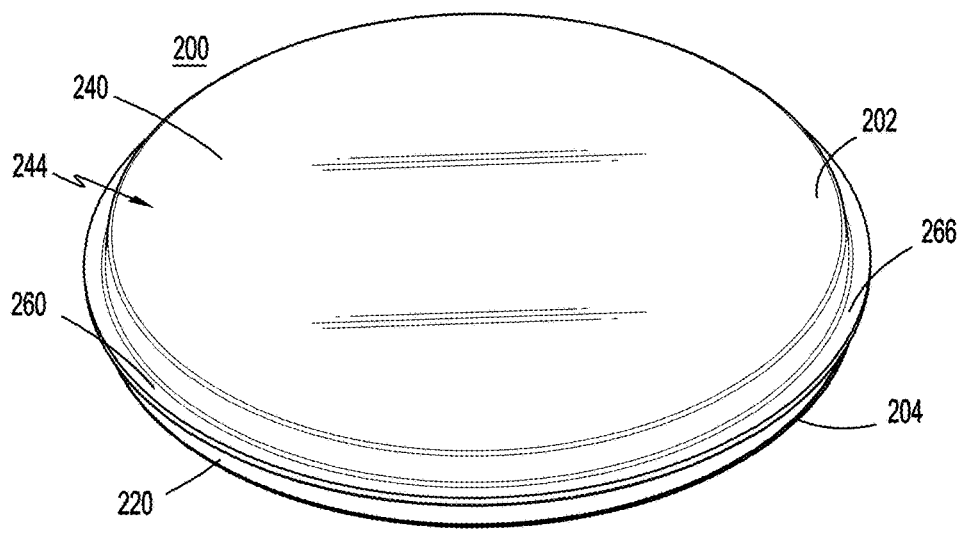
FIG. 9A is a top perspective view of the lid of the culture dish of FIG. 1 without markings.
Figure 9B:
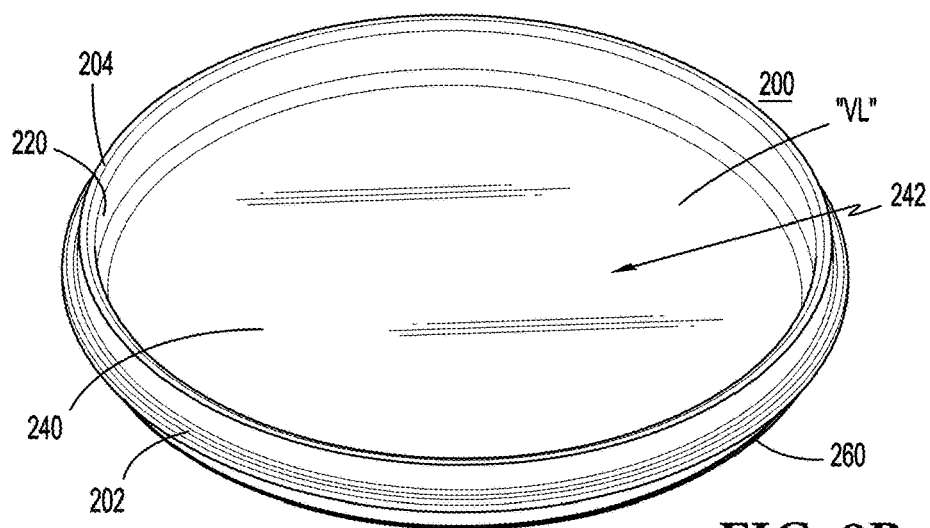
FIG. 9B is a bottom perspective view of the lid of the culture dish of FIG. 1.
Figure 10:
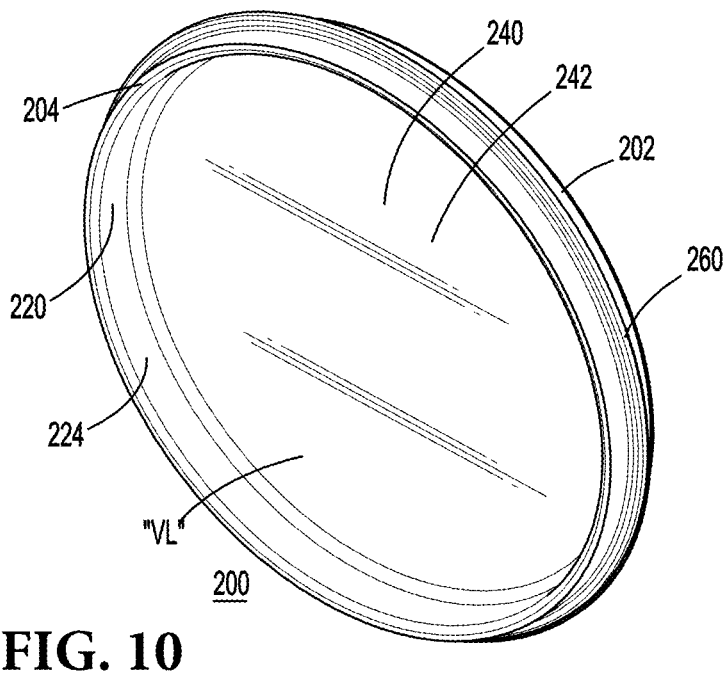
FIG. 10 is a side, perspective view of the lid of the culture dish of FIG. 1.
Figure 11:
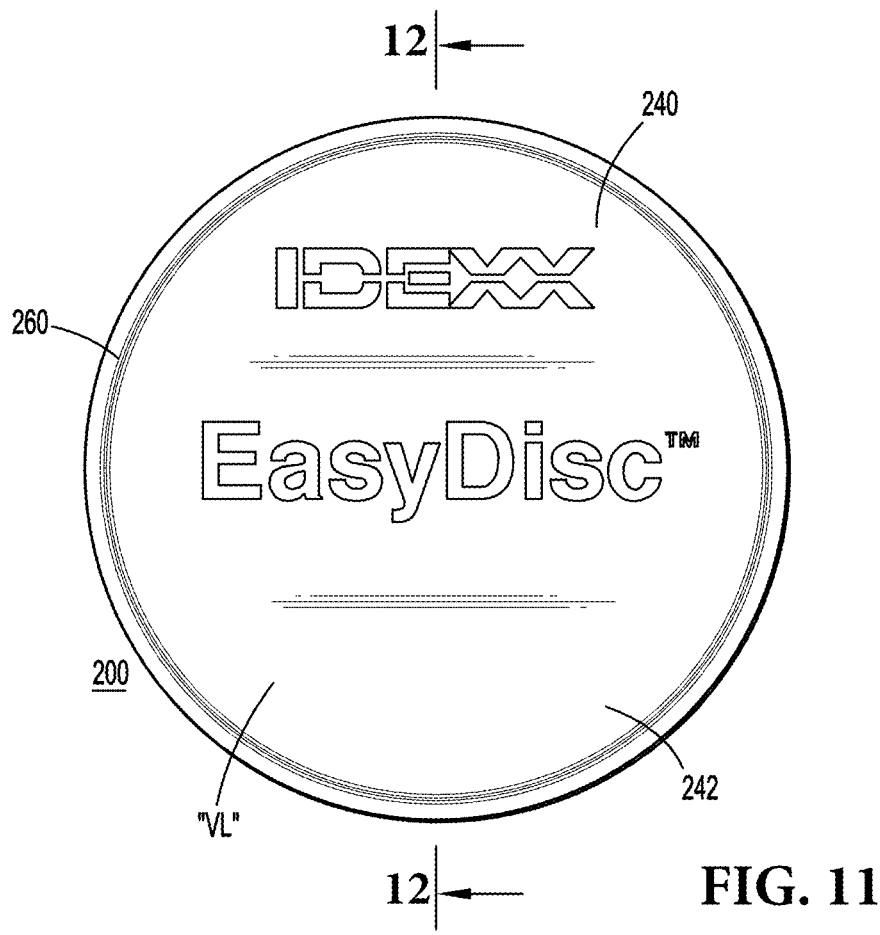
FIG. 11 is a top view of the lid of the culture dish of FIG. 1.

Referring to FIGS. 9-13, lid 200 of culture dish 10 is configured to releasably sealingly engage base 100 (FIGS. 1-8). Lid 200 is formed as a single, monolithic piece of material from molding or other suitable process. Lid 200 is opaque and may achieve opaqueness through opaque pigment throughout the material forming lid 200. Alternatively, lid 200 may achieve opaqueness via frosting, painting, stickering, etc. at least a portion of lid 200. As shown in FIG. 9, lid 100 may include markings conveying product information, e.g., product name, manufacturer name, etc., and/or markings conveying other information for tracking, identifying, etc. different culture dishes 10, e.g., numbers, letters, etc. The markings may be raised markings extending from ceiling 240 of lid 200 (as shown), or may be etched, molded into, drawn, transferred, printed, or otherwise formed on ceiling 240 of lid 200 (and/or any other suitable portion of culture dish 10). Alternatively, as shown in FIG. 9A, markings may be omitted.

In embodiments, lid 200 is white to provide contrast with bacterial colonies growing within base 100. The growth medium may contain a color indicator reagent that colors the colonies, e.g., red blue, etc., to increase contrast and make the colonies more easily visible against the white background of lid 200. However, while white provides good contrast for viewing certain bacterial colonies, e.g., indicator colors red, blue, etc., other opaque colors can be chosen depending on the color of the bacterial colonies. For example, substantially colorless colonies may be better viewed against a darker background and, thus, lid 200 may be a darker color to provide such contrast. In other embodiments, lid 200 is formed from an optically clear material and is set on and/or against an opaque, e.g., white or dark-color, background separate from lid 200. Further, lid 200, in embodiments, may include a grid pattern (not shown) thereon, e.g., on ceiling 240, of a different color, darkness, texture, etc., that is visible when viewed through base 100. The grid pattern facilitates the determination of the number of colonies per unit surface area. Additionally or alternatively, base 100 (FIGS. 1-8) may include a grid pattern. Whether provided on base 100 (FIGS. 1-8) and/or lid 200, the grid pattern may be disposed on an inside and/or outside surface of the base 100 (FIGS. 1-8) and/or lid 200 and may be laser etched, molded into, drawn, transferred, printed, etc., onto the surface(s). Further still, base 100 (FIGS. 1-8), lid 200, or the assembled culture dish 10 may be placed on a surface or carrier having a grid pattern thereon for similar purposes.

Lid 200 is formed from a relatively flexible material to enable lid 200 be deformed and/or stretched over base 100 in sealing engagement therewith, as detailed below. "Flexible" as utilized herein includes any combination of deformation, e.g., permanent or elastic, properties. That is, flexibility may be provided by softness, e.g., low hardness, that enables permanent deformation to sealingly engage base 100, and/or compliance, e.g., high elongation number, that enables elastic deformation to sealing engage base 100. Further, the materials forming lid 200 and base 100 are selected to achieve a sealed, sufficiently secure interference fit engagement therebetween, as detailed below. This is accomplished by selecting materials for lid 200 and base 100 that cooperate to have a suitable coefficient of fiction and mating engagement. The "seal" established between base 100 and lid 200 is a direct-contact seal, e.g., wherein the material forming the base 100 and the material forming the lid 200 directly contact and interact to achieve a seal, formed as a result of the configuration of lid 200 and base 100 as detailed herein. The seal may be a hermetic seal, a liquid-impervious seal, or other suitable seal.

In embodiments, the material forming lid 200 has a "high" oxygen permeability while having a "low" permeability for water vapor. Oxygen permeability may be beneficial in promoting the growth of aerobic microbes or facultatively aerobic microbes. A "high" oxygen permeability of lid 200 for the purposes herein is considered an oxygen transmission rate, measured in 25 µg/m$^2$/24 h, in embodiments, of at least 4000, in other embodiments, of at least 6000, and in still other embodiments, of at least 8000. Alternatively, the "high" oxygen permeability of lid 200 may be in-line with that of base 100 (FIGS. 1-8). A "low" permeability for water vapor of lid 200 for the purposes herein is considered a water vapor transmission rate, measured in 25 µg/m²/24 h, in embodiments, of no greater than 100, in other embodiments, no greater than 50, and in still other embodiments, no greater than 25. Alternatively, the "low" permeability for water vapor of lid 200 may be in-line with that of base 100 (FIGS. 1-8). Further, in embodiments, the material forming base 100 has a relatively high oxygen permeability and a relatively low permeability for water vapor, wherein such relativity for the purposes herein is considered a ratio of oxygen permeability to water vapor permeability of, in embodiments, of at least 100:1, in other embodiments, at least 200:1 and, in still other embodiments, at least 400:1 or, alternatively, may be in-line with that of base 100 (FIGS. 1-8). One suitable material meeting the above criteria is flexible, low density polyethylene (LDPE), although other suitable materials are also contemplated, e.g., plastics that have a rubber component.

As an alternative to the above-detailed material properties of base 100 (FIGS. 4A-8) and lid 200, such may be reversed, e.g., wherein base 100 (FIGS. 4A-8) is formed from a flexible material such as LDPE and lid 200 is formed from a hard material such as polystyrene.

Continuing with reference to FIGS. 9-13, lid 200 defines a top end 202 and a bottom end 204 and includes a side wall 220, a ceiling 240, and an annular rim 260. Side wall 220 defines a generally cylindrical configuration and is open at bottom end 204 of lid 220. Ceiling 240 disposed at top end 202 and extends across side wall 220 to enclose top end 202 of lid 200. Bottom end 204 of lid 200 is open to an internal volume "VL" defined by sidewall 220. Annular rim 260 extends from side wall 220 at a position towards but spaced-apart from top end 202 of lid 200.

Figures 12, 13:
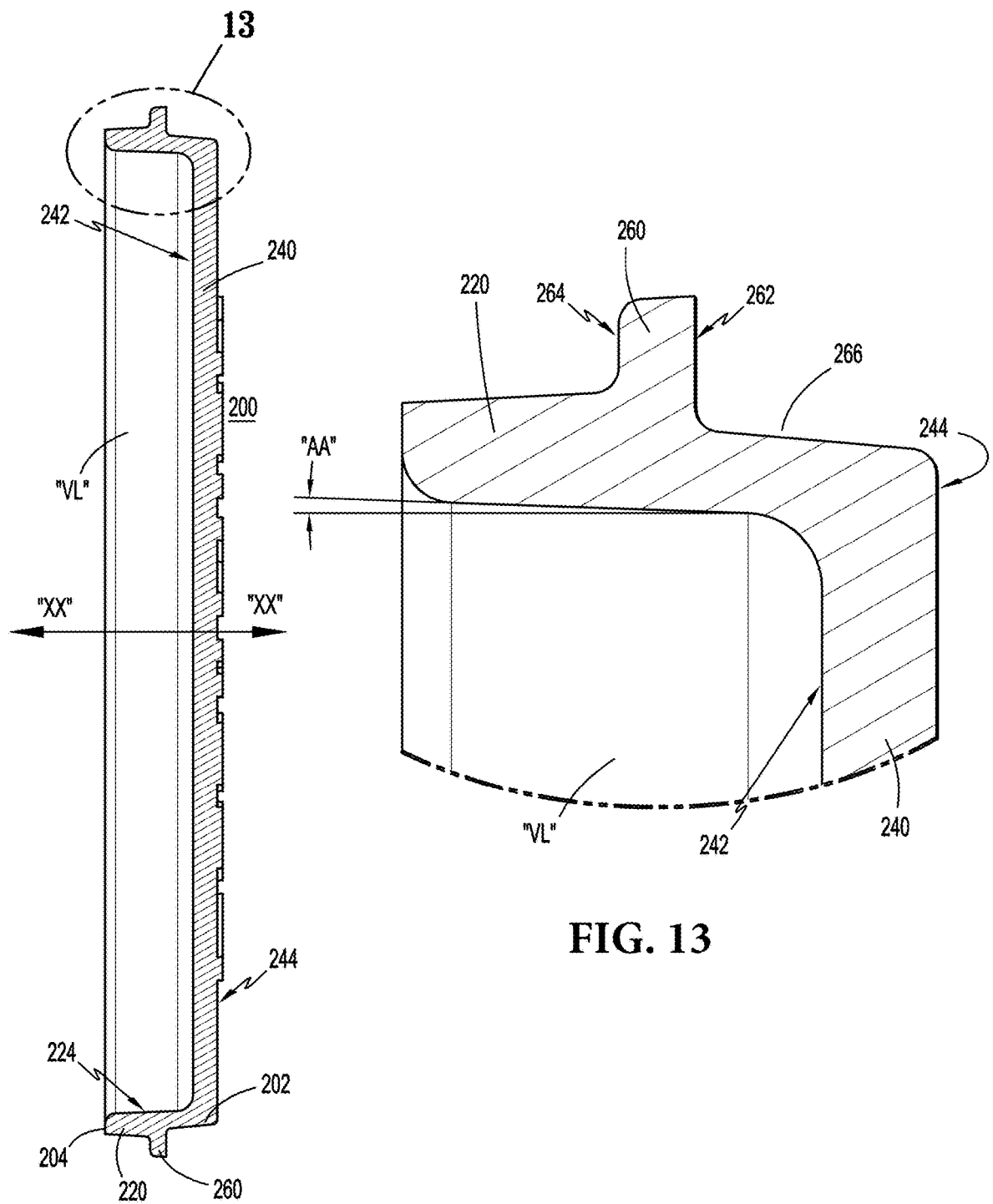
FIG. 12 is a cross-sectional view taken along section line "12-12" of FIG. 11.
FIG. 13 is an enlarged, cross-sectional view of the area of detail indicated as "13" in FIG. 12.

With reference in particular to FIGS. 12 and 13, side wall 220, as noted above, defines a generally cylindrical configuration. Side wall 220 surrounds a cylindrical internal volume "VL" having a circular transverse cross-section. However, side wall 220 is not perfectly cylindrical, in embodiments. Rather, in such embodiments, inner annular surface 224 of side wall 220 tapers radially outwardly in a top-to-bottom direction along at least a portion of the length of side wall 220, e.g., from top end 202 to bottom end 204 of lid 200, such that inner annular surface 224 of side wall 220 is angled relative to (rather than parallel to) the longitudinal axis "XX" of lid 200. More specifically, inner annular surface 224 of side wall 220 is angled radially outwardly off of parallel at an angle "AA" in a top-to-bottom direction. The angle "AA," in embodiments, may be from 1 degree to 3 degrees, in embodiments, from 1.5 degrees to 2.5 degrees and, in still other embodiments, 2 degrees. Further, the angle "AA" may be, in embodiments, from 0.5 degrees to 1.5 degrees, in other embodiments, from 0.75 degrees to 1.25 degrees and, in still other embodiments 1 degree less than the angle "A" defined between outer annular surface 122 of side wall 120 of base 100 and the longitudinal axis "X" of base 100 (see FIG. 8). This configuration facilitates a robust sealed engagement between lid 200 and base 100, as detailed below. It is noted that longitudinal axes "X" and "XX" are coaxial with one another, although other configurations are also contemplated.

Referring again to FIGS. 9-13, ceiling 240 of lid 200, as noted above, is disposed at top end 202 of lid 200 and extends across side wall 220 to enclose top end 202 of lid 200. Ceiling 240, more specifically, defines a generally planar, circular-shaped configuration; however, due to the flexible configuration of lid 200, ceiling 240 may not be perfectly planar; that is, ceiling 240 may define a convex, concave, or other non-planar configurations, depending upon forces and/or pressures acting thereon. Ceiling 240 defines an inner surface 242 that faces towards bottom end 204 of lid 200 and defines a top-end boundary of the internal volume "VL" defined by inner annular surface 224 of side wall 220 at top end 202 of lid 200. Ceiling 240 further defines an outer surface 244 opposite inner surface 242 and defining a portion of the exterior of lid 200. Bottom end 204 of lid 200 is open, thus providing access to the internal volume "VL."

As illustrated in FIG. 13, annular rim 260, as noted above, extends from side wall 220 towards but spaced-apart from top end 204 of lid 200. In this manner, a ring-shaped recess 266 is disposed atop a top-end-facing surface 262 of annular rim 260 and about ceiling 240. Annular rim 260 further defines a bottom-end-facing surface 264 opposite top-end-facing surface 262.

Referring generally to FIGS. 1-13, the above-detailed configuration of culture dish 10 facilitates manipulation of lid 200 and base 100 (as separate components and when engaged with one another), pouring a test sample (and/or growth medium) into base 100, sealing engagement of lid 200 with base 100, disengagement of lid 200 from base 100, stacking of plural culture dishes 10 atop one another, incubation, and counting the number of resultant bacterial colonies after incubation (although other testing methods are also contemplated).

With respect to manipulation, engagement, and disengagement, annular rims 160, 260 of base 100 and lid 200, respectively, protrude from respective side walls 120, 220 to provide finger holds for a user to grasp and manipulate base 100 and lid 200, respectively, without slipping. The annular configuration of annular rims 160, 260 provides such finger holds about the entire outer perimeters of base and lid 200. The above-detailed configuration of finger holds formed by annular rims 160, 260 enables one-handed manipulation, engagement, and disengagement of base 100 and lid 200. More specifically, one-handed engagement and disengagement may be accomplished as follows: one or more fingers of the hand are used to engage annular rim 160 or another of base 100 to hold or otherwise stabilize base 100, e.g., against a table or other support structure, while another finger or fingers of the same hand are used to engage annular rim 260 or another portion of lid 200 to engage lid 200 with base 100 or disengage lid 200 from base 100. Further, with regard to disengagement, lifting lid 200 on only one side, e.g., angling lid 200 upwardly on one side while the opposite side initially remains in contact and at least partial engagement with base 100, may be sufficient to create an opening to enable the addition of the sample, e.g., with a pipette held with the opposite hand.

With respect to sealing engagement of lid 200 about base 100, more specifically, lid 200, led by bottom end 204 thereof, and/or base 100, led by top end 102 thereof, are approximated relative to one another such that side wall 220 of lid 200 is slid about side wall 120 of base 100. A maximum, minimum, or average diameter of inner annular surface 224 of side wall 220 of lid 200 may be equal to a respective maximum, minimum, or average diameter of outer annular surface 122 of side wall 120 of base 100. This, together with the flexibility of lid 200 and the difference between angle "A" (FIG. 8) and angle "AA" (FIG. 13) helps establish a robust sealed engagement between lid 200 and base 100, wherein the seal and engagement is increasingly tightened as side wall 220 of lid 200 is slid further about side wall 120 of base 100 (and lid 200 is further flexed) to a fully engaged position.

Figure 17:
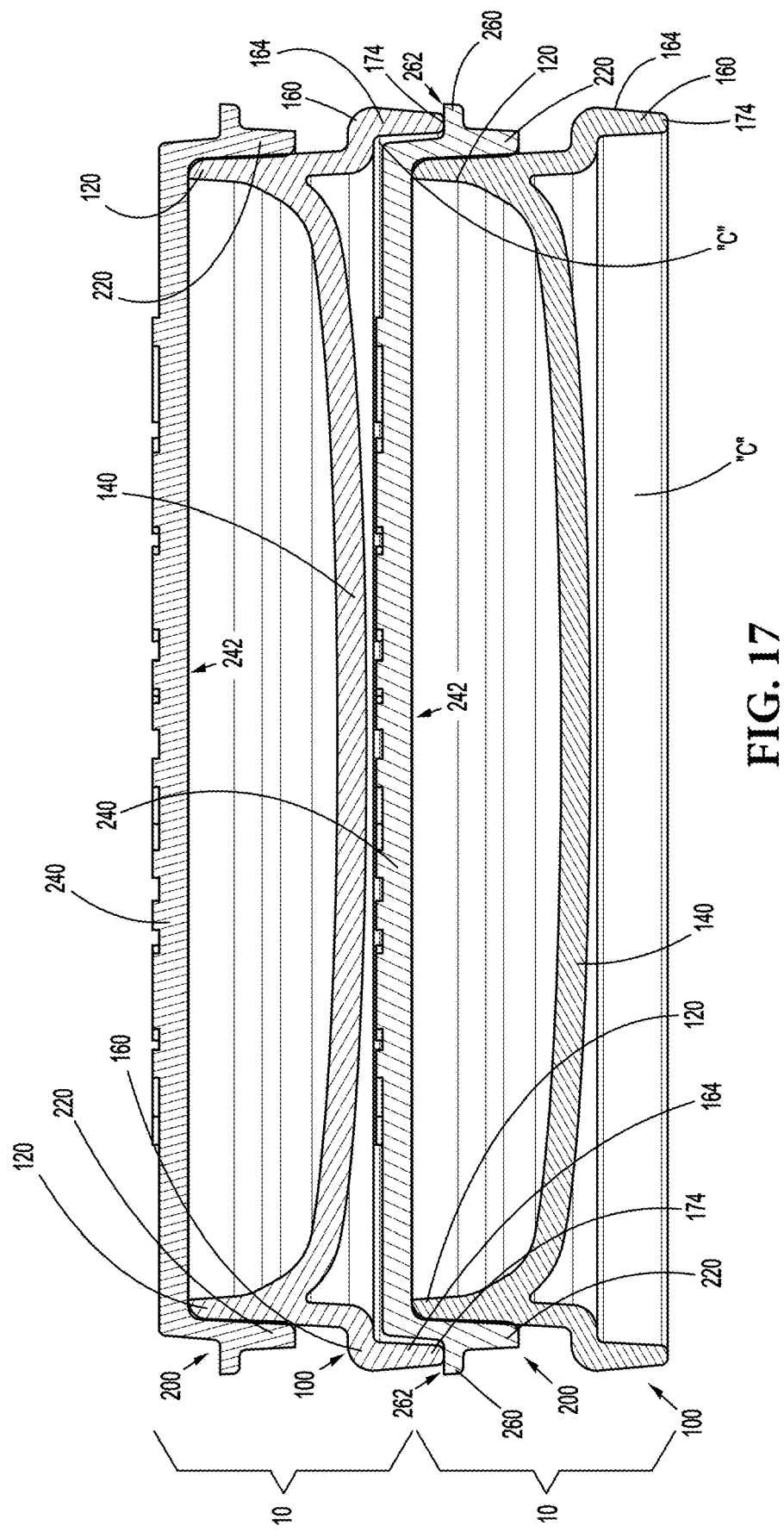
FIG. 17 is a transverse, cross-sectional view taken along section line "17-17" of FIG. 16.
Figure 18A:
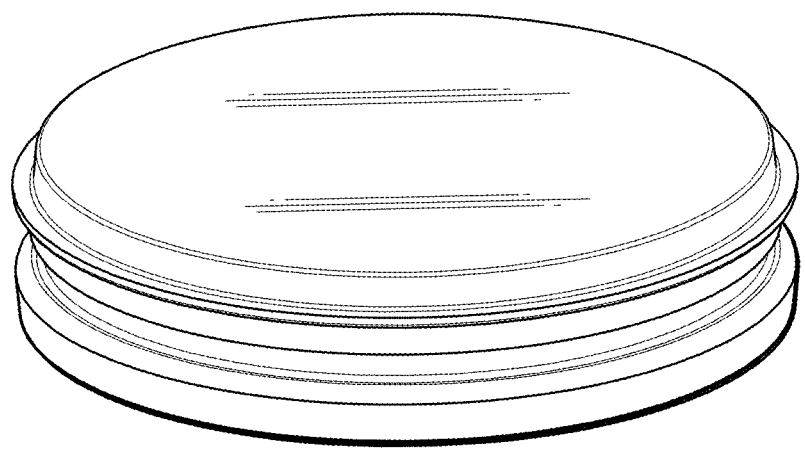
FIGS. 18A-18E are top perspective, bottom perspective, top, bottom, and side views, respectively, of the culture dish of FIG. 1.
Figure 18B:
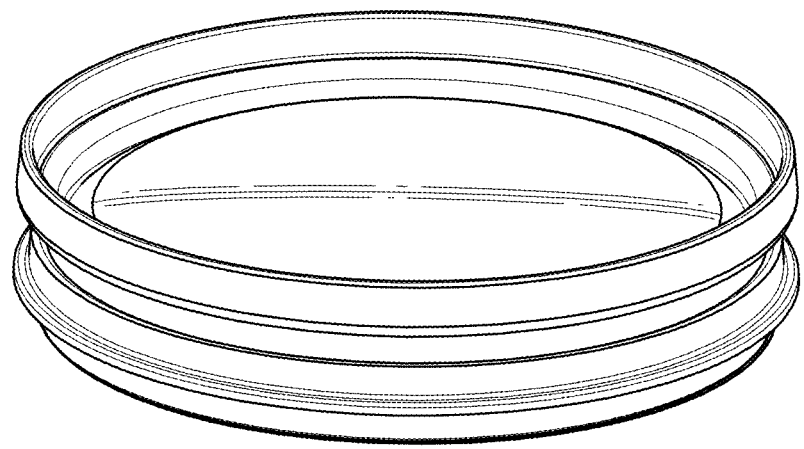
Figure 18C:
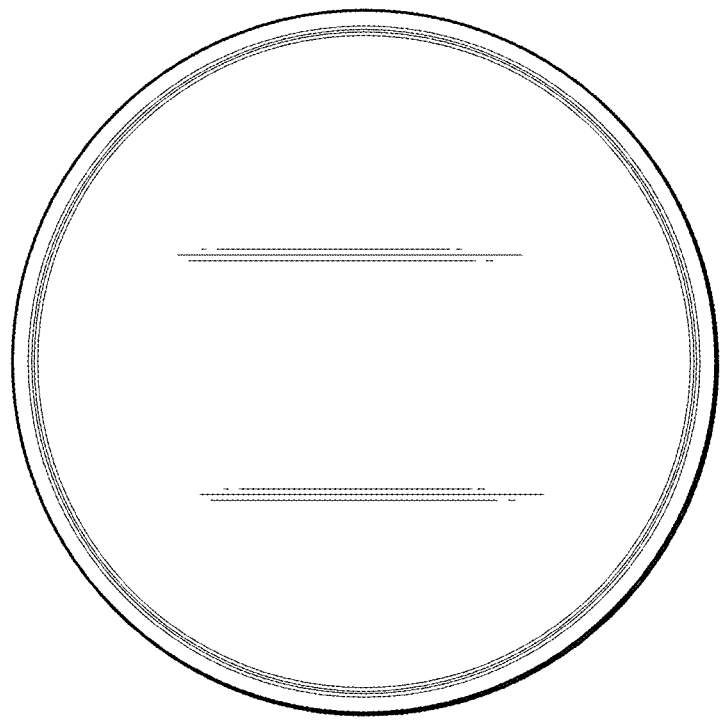
Figure 18D:
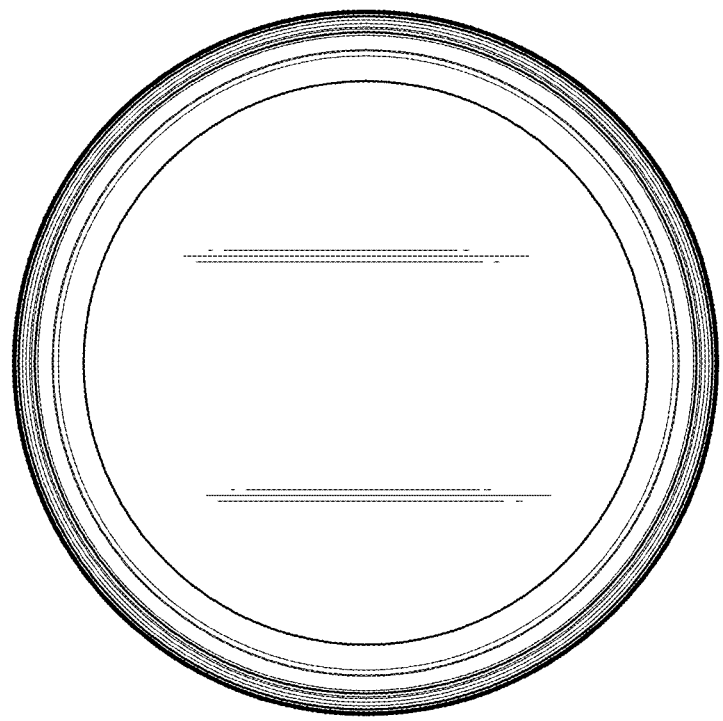
Figure 18E:
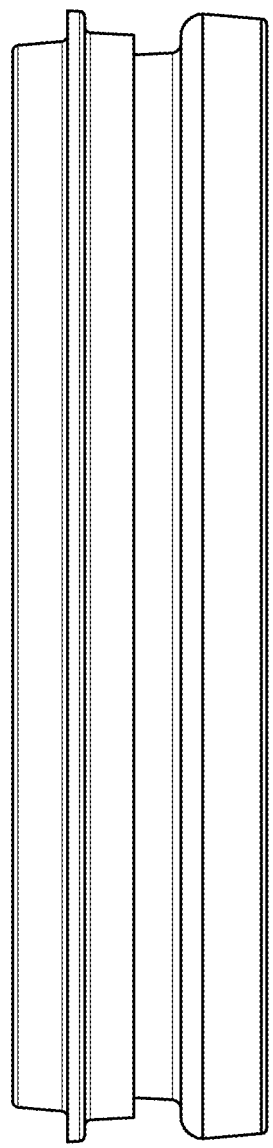
Figure 19A:
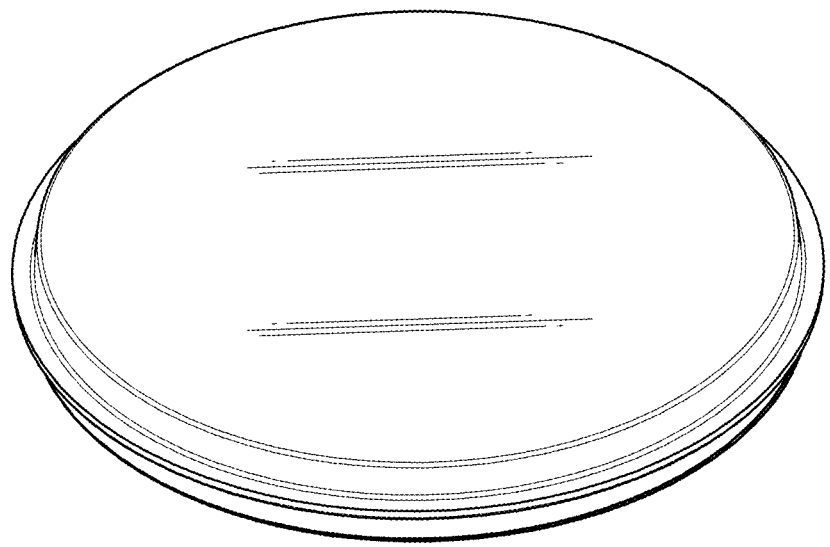
FIGS. 19A-19E are top perspective, bottom perspective, top, bottom, and side views, respectively, of the lid of the culture dish of FIG. 1.
Figure 19B:
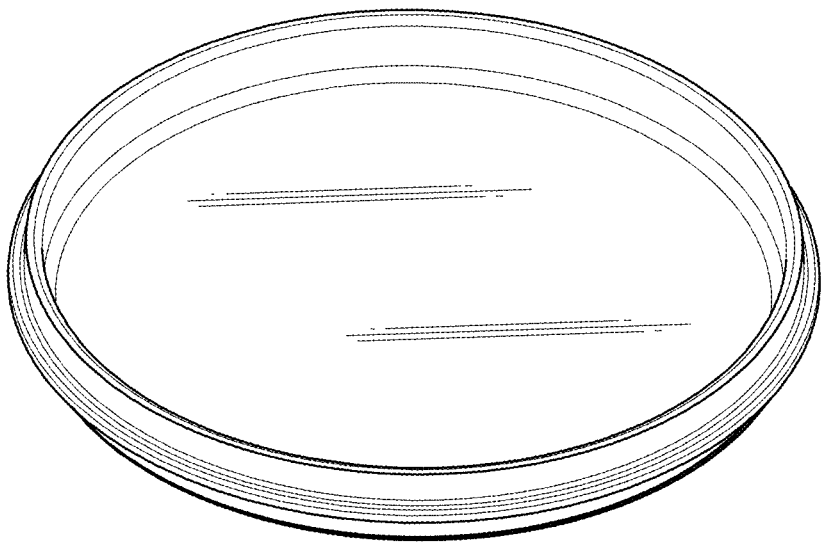
Figure 19C:
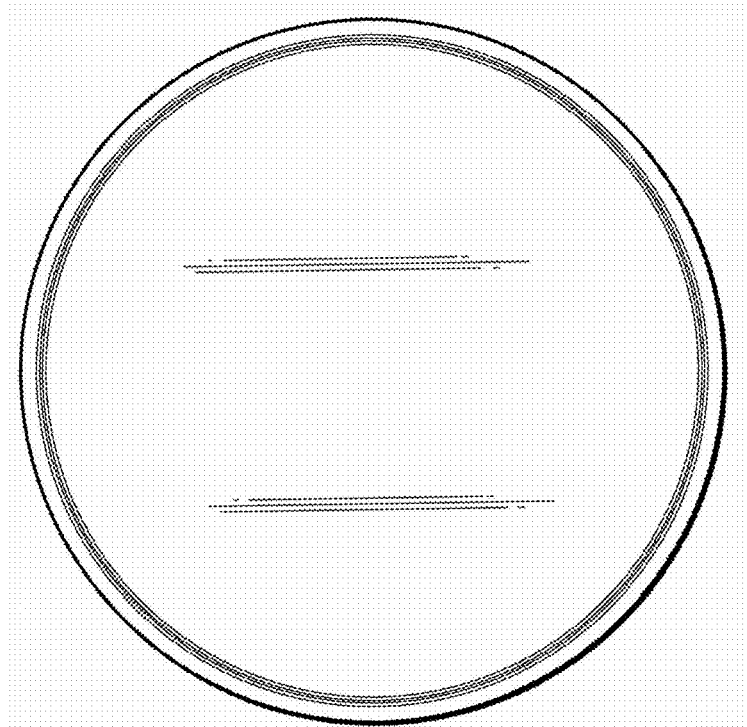
Figure 19D:
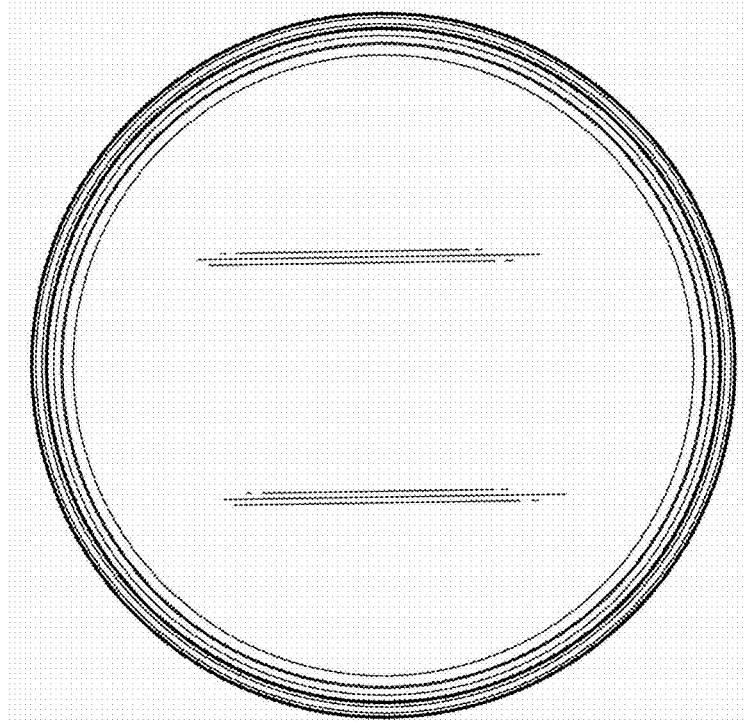
Figure 19E:
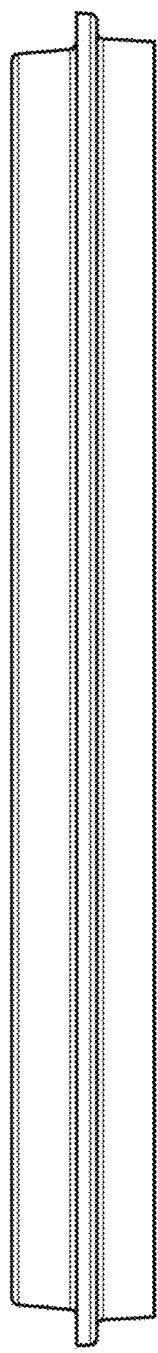
Figure 20A:
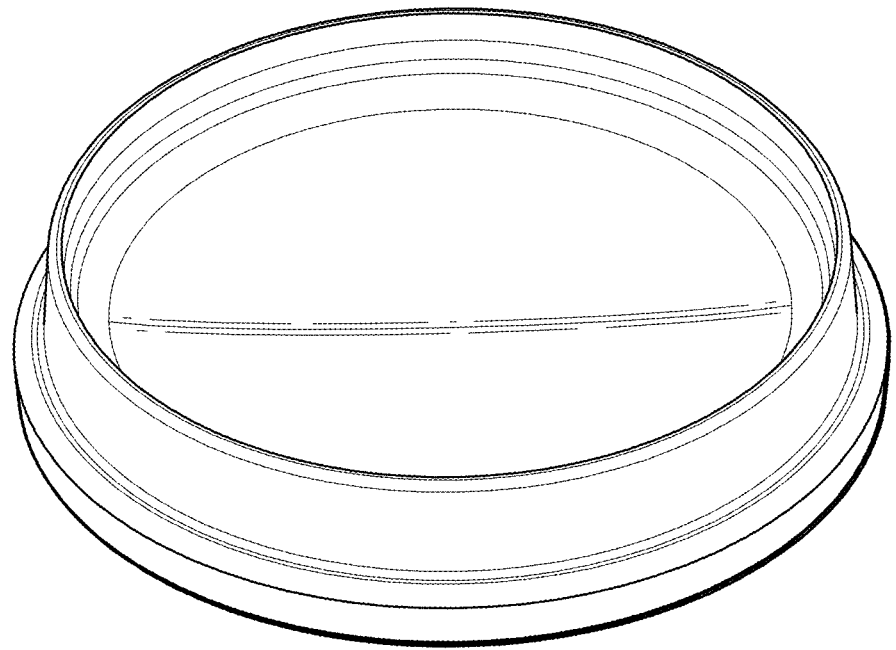
FIGS. 20A-20E are top perspective, bottom perspective, top, bottom, and side views, respectively, of the base of the culture dish of FIG. 1.
Figure 20B:
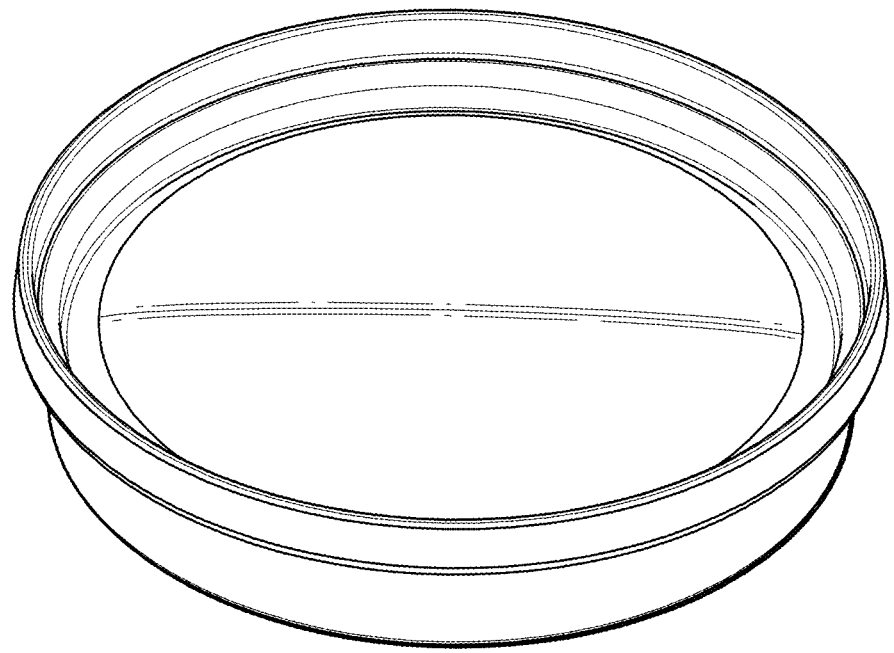
Figure 20C:
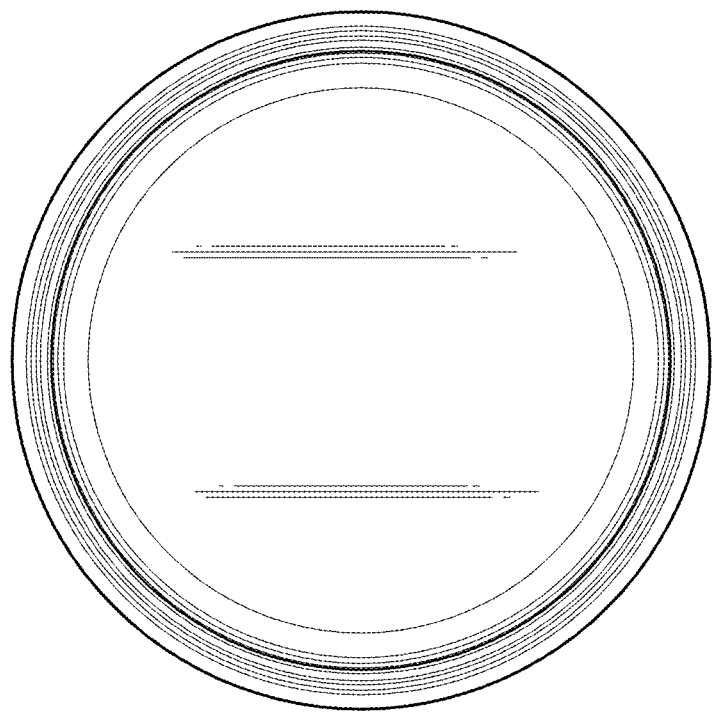
Figure 20D:
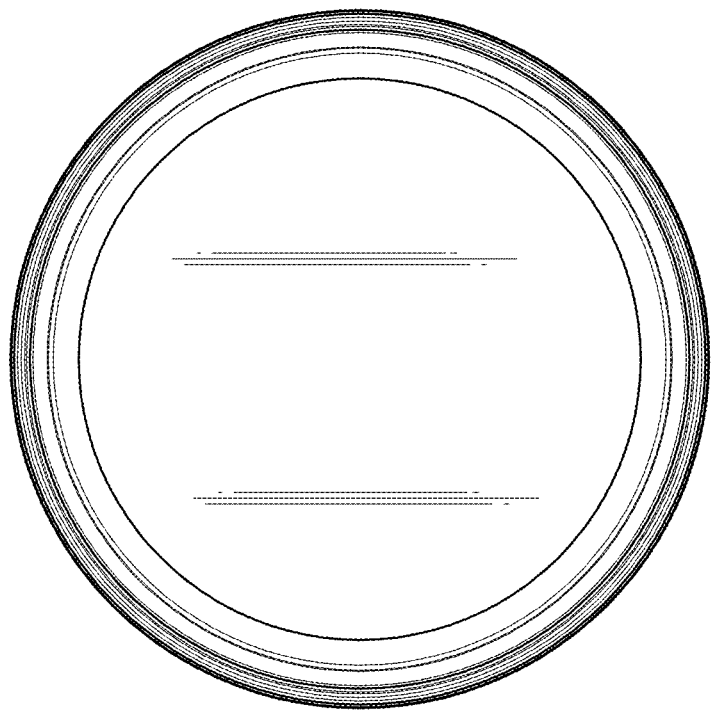
Figure 20E:
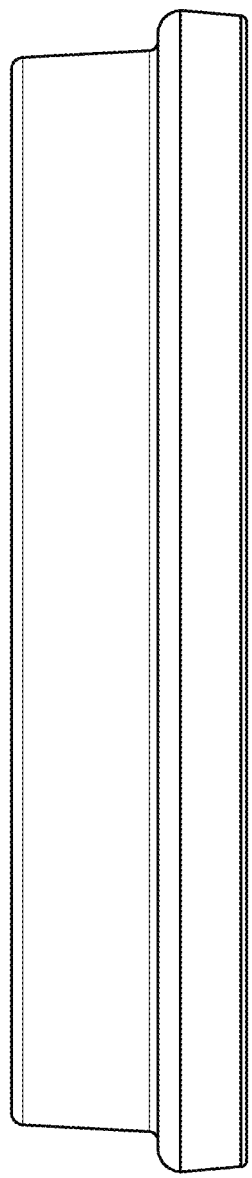

With additional momentary reference to FIG. 17, in the fully engaged position, the top end edge of side wall 120 of base 100 may abut inner surface 242 of ceiling 240 of lid 200 and/or the bottom end edge of side wall 220 of lid 200 may abut the exterior surface of annular shelf 170 of annular rim 160 of base 100. The desired abutment(s) may be achieved by varying the relative heights of side walls 120, 220 such that the abutment is provided between side wall 120 and ceiling 240, between side wall 220 and annular shelf 170, or between both side walls 120, 220 and ceiling 240 and annular shelf 170, respectively (e.g., substantially simultaneously). The abutment(s), e.g., between side wall 120 and ceiling 240 and/or between side wall 220 and annular shelf 170, defines a bottomed-out condition, corresponding to the fully engaged position, that inhibits further approximation of base 100 and lid 200 relative to one another. In embodiments where side wall 220 of lid 200 defines a reduced height as compared to side wall 120 base 100, such that, in the bottomed-out condition (the fully engaged position), side wall 120 abuts ceiling 240 and a spacing is defined between side wall 220 and annular shelf 170. In this bottomed-out condition, less overlapping annular surface contact between lid 200 and base 100 is provided (as compared to embodiments where the height of side wall 220 relative to the height of side wall 120 is increased), thus reducing the force required to remove lid 200. In the bottomed-out condition, corresponding to the fully engaged position, interior volumes "VB" and "VL" are in overlapping communication with one another to define a collective sealed interior volume "VS" within culture dish 10.

In embodiments, the sealed interior volume "VS" defined within culture dish 10 with lid 200 sealed about base 100 in the bottomed-out condition, in embodiments, is from about 5 mL to about 10 mL; in other embodiments, from about 6 mL to about 9 mL; and in still other embodiments, from about 7 mL to about 8 mL. An about 1 mL sample and/or an about 3.5 mL reagent within the culture dish 10 may be utilized with the above-noted volume ranges, although other sample volumes, reagent volumes, and/or sealed volumes "VS" are also contemplated.

With respect to the above volumes and/or other suitable volumes, sealed interior volume "VS" of culture dish 10 may define a maximum inner diameter of, in embodiments, from about 40 mm to about 48 mm; in other embodiments, from about 42 mm to about 46 mm; and in still other embodiments from about 43 mm to about 45 mm. An about 1 mL sample and/or an about 3.5 mL reagent within the culture dish 10 may be utilized with the above-noted diameter ranges, although other sample volumes, reagent volumes, and/or diameters are also contemplated.

With respect to the above volumes and/or other suitable volumes, sealed interior volume "VS" of culture dish 10 may define a maximum inner height of, in embodiments, from about 4 mm to about 8 mm; in other embodiments, from about 5 mm to about 7 mm; and in still other embodiments from about 5.5 mm to about 6.5 mm. An about 1 mL sample and/or an about 3.5 mL reagent within the culture dish 10 may be utilized with the above-noted height ranges, although other sample volumes, reagent volumes, and/or diameters are also contemplated.

Further, a ratio of the sealed interior volume "VS" to the volume of sample may be from about 5 to about 10 in embodiments; in other embodiments, from about 6 to about 9; and in still other embodiments, from about 7 to about 8. A ratio of the sealed interior volume "VS" to the volume of the reagent may be from about 1.4 to about 2.8, in embodiments; in other embodiments, from about 1.8 to about 2.4; and in still other embodiments, from about 2.0 to about 2.2. Additionally or alternatively, the present disclosure contemplates ratio ranges of the sample and/or reagent volumes, collectively or separately, relative to the volume, maximum height, and/or maximum width of the sealed interior volume "VS" of culture dish 10, as can be readily calculated from the above.

Again with general reference to FIGS. 1-13, the above-detailed engagement of lid 200 about base 100 resists opening, e.g., when culture dish 10 is dropped. As can be appreciated, this helps prevent both loss of sample and dissemination of microorganism that have amplified in number.

With respect to pouring the test sample (and/or growth medium) into base 100, as detailed above, concave bottom surface 142 of floor 140 of base 100 facilitates pouring and distributing the test sample (and/or growth medium) about floor 140 of base 100 by inhibiting or reducing meniscus formation resulting in uneven distribution and build up about the annular perimeter, e.g., against inner annular surface 124. Likewise, base 100 is configured to enable a 1 mL sample, e.g., water, to be poured and evenly distributed therein, as also detailed above.

Figure 15:
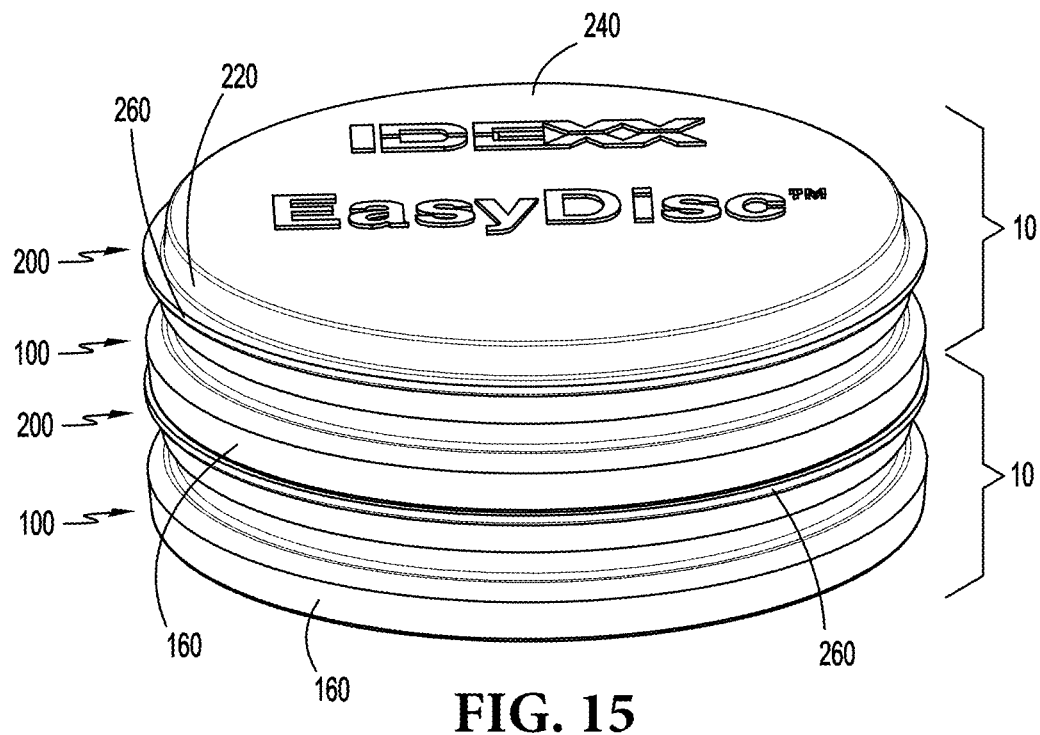
FIG. 15 is a side, perspective view illustrating two culture dishes in accordance with the present disclosure stacked on top of one another.
Figure 16:
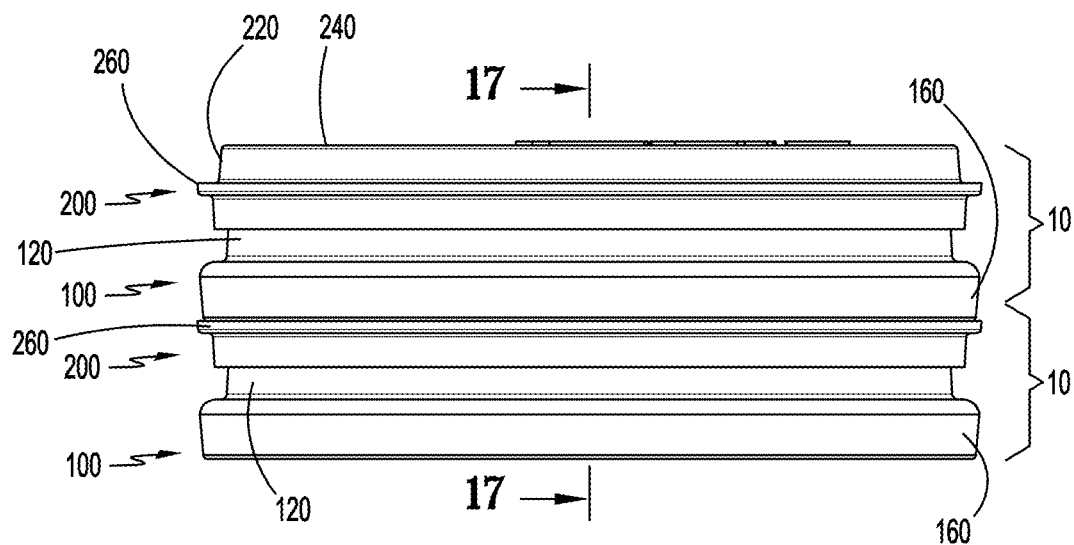
FIG. 16 is a side view of the stacked culture dishes of FIG. 15.

Turning to FIGS. 15-17, in order to stack two or more culture dishes 10, the base 100 of an upper culture dish 10 is approximated relative to the lid 200 of a lower culture dish such that the free end 174 of the longitudinal portion 164 of the annular rim 160 of the base 100 of the upper culture dish 100 is seated on the top-end-facing surface 262 of the annular rim 260 of the lid 200 of the lower culture dish 10. In this manner, the cylindrical area "C" defined within the bottom end 104 of the base 100 of the upper culture dish 100 receives the ceiling 240 of the lid 200 of the lower culture dish 100 therein. The ceilings 240 of the lids 200 may define outer diameters that generally approximate the diameters of the cylindrical areas "C" of the bases 100 such that minimal play is defined therebetween in a stacked configuration of two or more culture dishes 10. The above-detailed configuration enables stable stacking of multiple culture dishes 10 on top of one another.

Returning with general reference to FIGS. 1-13, with respect to incubation, the sealed engagement between lid 200 and base 100 prevents evaporation of the water (or other) sample from the growth medium during incubation. This is particularly important given the relatively small volume of sample contemplated for use: 1 mL of test sample, e.g., water, and becomes more important the longer the incubation period. For example, incubation of a water sample on R2A growth medium may require 7 days. Further, the high or relatively high oxygen permeability and low or relatively low permeability for water vapor of base 100 and lid 200 may be beneficial in promoting the growth of aerobic microbes or facultatively aerobic microbes.

With respect to counting the number of resultant bacterial colonies after incubation, the optically clear base 100 allows visualization therethrough into the interior of base 100, while the opaque, e.g., white, lid 200 provides a backdrop with suitable contrast to facilitate counting. Additional features of lid 200 may further enhance counting ability, such as those detailed above. Counting may additionally or alternatively be performed with the lid 200 removed from the base 100.

Turning to FIG. 14, in conjunction with FIGS. 1-3, a method provided in accordance with the present disclosure includes providing a culture dish, e.g., culture dish 10. It is contemplated that culture dish 10 includes a growth medium disposed therein during manufacturing, lid 200 is sealingly engaged about base 100 with the growth medium therein, and culture dish 10 is wrapped or otherwise packaged for transport, storage, etc. until ready for use. With respect to disposing the growth medium within base 100 during manufacturing, more specifically, the growth medium may be added to the base 100 as a fluid, allowed to cool to form a gel, and then dried (dehydrated) to floor 140 of base 100. The growth medium may be an R2A (Reasoner's 2A Agar) growth medium or other suitable growth medium such as, for example: YEA (Yeast Extract Agar), PCA (Plate Count Agar), or SMA (Standards Methods Agar).

The method further includes unwrapping and/or removing packaging from about the culture dish and removing the lid from the culture dish, e.g., by grasping annular rim 160 of base 100 and/or annular rim 260 of lid 200 and pulling base 100 and/or lid 200 apart from one another.

Once the lid is removed, a test sample is poured into an interior volume of the base of the dish and, e.g., evenly distributed therein due to the configuration of floor 140 of base 100. If the growth medium is not already disposed within base 100, e.g., in embodiments where the growth medium is not dried to floor 140 of base 100 during manufacturing, the growth medium may likewise be poured into base 100 before, after, or overlapping with the pouring of the sample. With respect to culture dish 10 in particular, base 100 is configured such that a 1 mL sample, e.g., of water, poured into the interior volume "VB" of base 100 is evenly distributed about floor 140 of base 100. However, other sample sizes and configurations are also contemplated. The sample, e.g., water or other suitable sample, may be agitated to spread the sample about the growth medium. When the 1 mL water sample is poured into base 100, the water interacts with the dried growth medium to reconstitute (rehydrate) it. Although detailed hereinbelow with respect to a water sample, it is understood that the same or similar methods may be utilized for testing other samples such as those noted above.

With the growth medium and water sample in the base (and the growth medium reconstituted by the water sample), the lid of the culture dish is sealingly engaged about the base to enclose and seal the water sample and growth medium therein, e.g., via the sliding, sealed interference fit engagement of side wall 220 of lid 200 about side wall 120 of base 100. Once sealed, the culture dish may be inverted and placed to rest on the lid. Alternatively, the culture dish may be placed to rest on base 100 in a non-inverted orientation. Multiple culture dishes may be stacked on top of one another, similarly as detailed above with respect to culture dish 10. The sealed culture dish is then incubated for a suitable time and under suitable conditions to support growth.

After incubation, the number of bacterial growth colonies are counted against the backdrop of the lid to determine the presence or absence of microbial organisms in the water sample. More specifically, with respect to culture dish 10, a user can look through the optically clear base 100 and count the number of bacterial growth colonies using the white, opaque lid 200 as a contrast-providing backdrop. Inverting the culture dish 10 (if not already done so for incubation) may, in some instances, be performed to facilitate counting; in other instances, culture dish 10 need not be inverted. Counting may additionally or alternatively be performed with the lid 200 removed from the base 100.

The methods detailed hereinabove may further include waiting period(s) between some or all of the actions. For example, a sufficient waiting period after agitating the sample and prior to sealingly engaging the lid and/or a sufficient waiting period after sealingly engaging the lid and prior to inverting the seal culture dish may be implemented to enable the sample/growth medium mixture to set, gel, cool-off, etc. Additional or alternative waiting periods may be implemented between other actions for similar or different purposes.

It is understood that reference to any specific numerical value herein encompasses a range of values to take into account material and manufacturing tolerances generally accepted in the art and/or margins of error of measurement equipment generally accepted in the art.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:
1. A culture dish, comprising:
 a base defining a longitudinal axis and having a top end and a bottom end, the base including:
  a side wall extending from the top end of the base towards the bottom end of the base, the side wall including a top end defining a free edge, a bottom end, an annular inner surface defined from the top end to the bottom end, an annular outer surface defined from the top end to the bottom end;
  a floor directly connected to and supported by the annular inner surface of the side wall at a first location along the annular inner surface that is disposed between and longitudinally spaced apart from each of the free edge at the top end of the side wall and the bottom end of the side wall such that a first portion of the annular inner surface is defined from the free edge at the top end of the side wall to the floor and such that a second portion of the annular inner surface is defined from the floor to the bottom end of the side wall, the floor extending radially inwardly from the first location of the annular inner surface of the side wall and longitudinally towards the bottom end of the base, the floor having a concave surface facing the top end of the base and a convex surface facing the bottom end of the base, wherein the concave surface of the floor and the annular inner surface of the side wall define a first interior volume that is open at the top end of the base; and
  an annular rim directly connected to the bottom end of the side wall at a second location disposed between and longitudinally spaced apart from each of the first location and the bottom end of the base, the annular rim protruding radially outwardly from the second location at the bottom end of the side wall; and
 a lid defining a longitudinal axis and having a top end and a bottom end, the lid including:
  a side wall extending from the top end of the lid towards the bottom end of the lid, the side wall including an annular inner surface and an annular outer surface;

a ceiling disposed atop the side wall at the top end of the lid, the ceiling defining an inner surface facing the bottom end of the lid and an outer surface facing the top end of the lid, wherein the inner surface of the ceiling and the annular inner surface of the side wall define a second interior volume that is open at the bottom end of the lid; and an annular rim extending radially outwardly from the annular outer surface of the side wall, wherein the inner annular surface of the side wall of the lid is configured for slidable receipt about the outer annular surface of the side wall of the base to engage the lid about the base with the first and second interior volumes at least partially overlapping one another to define a sealed, combined internal volume bounded by the side walls of the base and the lid, the floor, and the ceiling.

2. The culture dish according to claim 1, wherein the base is formed from an optically clear material and the lid is formed from an opaque material.

3. The culture dish according to claim 1, wherein the base is formed from a relatively hard material and the lid is formed from a relatively flexible material.

4. The culture dish according to claim 1, wherein the annular rim of the base includes a radial portion extending radially outwardly from the side wall and a longitudinal portion extending longitudinally from the side wall to the bottom end of the base, the annular rim surrounding a cylindrical volume.

5. The culture dish according to claim 4, wherein an outer diameter of the annular rim of the lid is greater than an outer diameter of the ceiling to define a ring-shaped recess atop the annular rim of the lid and about the ceiling.

6. The culture dish according to claim 5, wherein the ceiling is configured for receipt within the cylindrical volume of the longitudinal portion of the annular rim of the base with the longitudinal portion of the annular rim of the base disposed within the ring-shaped recess of the lid to stack the base on the lid.

7. The culture dish according to claim 1, wherein the inner annular surface of the side wall of the lid is disposed at a first angle and wherein the outer annular surface of the side wall of the base is disposed at a second angle different from the first angle.

8. The culture dish according to claim 1, wherein the annular rims of the lid and base define finger holds configured to facilitate manipulation, engagement, and disengagement of the lid and base.

9. The culture dish according to claim 1, wherein, in a bottomed-out condition, corresponding to a fully engaged position of the lid about the base, at least one of: the free edge of the side wall of the base abuts the ceiling of the lid or the side wall of the lid abuts the annular rim of the base.

10. The culture dish according to claim 1, wherein, in a bottomed-out condition, corresponding to a fully engaged position of the lid about the base, the free edge of the side wall of the base abuts the ceiling of the lid and the side wall of the lid is spaced from the annular rim of the base.

11. A culture dish, comprising:
a base defining a longitudinal axis and having a top end and a bottom end, the base including a side wall including annular inner and outer surfaces defined from the top end of the base to a first location disposed between and spaced apart from each of the top and bottom ends of the base and filling a volume defined between the annular inner surface and the annular outer surface from the top end of the base to the first location, the base further including a floor supported by the inner annular surface of the side wall at a second location disposed between and longitudinally spaced apart from each of the top end of the base and the first location; and
a lid defining a longitudinal axis and having a top end and a bottom end, the lid including a side wall including an annular inner surface and an annular outer surface, and a ceiling disposed atop the side wall at the top end of the lid,
wherein one of the base or the lid defines a relatively hard configuration and wherein the other of the base or the lid defines a relatively flexible configuration, and
wherein the inner annular surface of the side wall of the lid is configured for slidable contact with the outer annular surface of the side wall of the base to engage the lid about the base, thereby defining an internal volume bounded by the ceiling, the floor, and one of the annular inner surface of the side wall of the base or a portion of the annular inner surface of the side wall of the base in combination with a portion of the annular inner surface of the side wall of the lid, and wherein the relatively flexible one of the base or the lid is configured to flex to permit sliding of the lid about the base and to sealing engage the lid about the base to define the internal volume.

12. The culture dish according to claim 11, wherein the base defines a relatively hard configuration and the lid defines a relatively flexible configuration.

13. The culture dish according to claim 12, wherein the base is formed from hard polystyrene and the lid is formed from low density polyethylene.

14. The culture dish according to claim 11, wherein the base is formed from an optically clear material and the lid is formed from an opaque material.

15. The culture dish according to claim 11, wherein the base is formed from a material having a high oxygen permeability and a low permeability for water vapor.

16. The culture dish according to claim 11, wherein the lid is formed from a material having a high oxygen permeability and a low permeability for water vapor.

17. The culture dish according to claim 11, wherein at least one of the base or the lid includes an annular rim extending from the respective side wall thereof, the at least one annular rim defining a finger hold configured to facilitate manipulation, engagement, and disengagement of the at least one of the lid or the base.

18. The culture dish according to claim 11, wherein the base includes an annular rim extending from the side wall thereof and wherein the ceiling of the lid is configured for at least partial receipt within the annular rim of the base to stack the base on the lid.

19. The culture dish according to claim 11, wherein the inner annular surface of the side wall of the lid is disposed at a first angle and wherein the outer annular surface of the side wall of the base is disposed at a second angle different from the first angle.

20. A culture dish, comprising:
a base defining a longitudinal axis and having a top end and a bottom end, the base including a side wall defined by an annular inner surface and an annular outer surface, and a floor supported by the annular inner surface of the side wall at a location disposed between and longitudinally spaced apart from each of a top end and a bottom end of the annular inner surface; and
a lid having a top end and a bottom end, the lid including a side wall including an annular inner surface and an annular outer surface, and a ceiling disposed atop the side wall at the top end of the lid, wherein the inner annular surface of the side wall of the lid is configured for slidable receipt about the outer annular surface of the side wall of the base along the longitudinal axis to a bottomed-out condition, corresponding to a fully engaged position of the lid about the base, wherein a top edge of the side wall of the base abuts the ceiling of the lid, wherein the inner annular surface of the side wall of the lid is angled radially outwardly in a top to bottom direction along the longitudinal axis at a first angle relative to the longitudinal axis and wherein the outer annular surface of the side wall of the base is angled radially outwardly in the top to bottom direction along the longitudinal axis at a second angle relative to the longitudinal axis that is greater than the first angle such that increased sealing engagement between the lid and the base is established as the lid is moved towards the fully engaged position.

21. The culture dish according to claim 20, wherein one of the base or the lid defines a relatively hard configuration and wherein the other of the base or the lid defines a relatively flexible configuration, and wherein the relatively flexible one of the base or the lid facilitates sliding of the lid about the base to the fully engaged position.

22. The culture dish according to claim 21, wherein the base defines a relatively hard configuration and the lid defines a relatively flexible configuration.

23. The culture dish according to claim 20, wherein the base further includes an annular rim extending from the side wall thereof.

24. The culture dish according to claim 23, wherein the annular rim of the base includes a radial portion extending radially outwardly from the side wall and a longitudinal portion extending from the radial portion to the bottom end of the base.

25. The culture dish according to claim 23, wherein, in the fully engaged position, a bottom edge of the side wall of the lid is spaced from the annular rim of the base.

26. The culture dish according to claim 20, wherein the lid further includes an annular rim extending from the side wall thereof.

27. The culture dish according to claim 26, further comprising:
a second base having a top end and a bottom end, the second base including a side wall including an annular inner surface and an annular outer surface, a floor supported by the side wall at a position disposed between the top and bottom ends of the second base, and an annular rim extending from the side wall,
wherein a free bottom end of the annular rim of the second base is configured to sit on the annular rim of the lid to stack the second base on the lid, and
wherein, with the second base stacked on the lid, the ceiling of the lid is at least partially received within the annular rim of the second base in spaced-apart relation relative to the floor of the second base.

28. The culture dish according to claim 20, further comprising:
a second lid having a top end and a bottom end, the second lid including a side wall including an annular inner surface and an annular outer surface, a ceiling disposed atop the side wall at the top end of the second lid, and an annular rim extending from the side wall thereof,
wherein the bottom end of the base is configured to sit on the annular rim of the second lid to stack the base on the second lid.

29. The culture dish according to claim 28, wherein, with the base stacked on the second lid, the ceiling of the second lid is at least partially received within an internal volume defined within the base in spaced-apart relation relative to the floor of the base.

* * * * *